United States Patent [19]
Miller et al.

[11] Patent Number: 5,780,278
[45] Date of Patent: Jul. 14, 1998

[54] ICEA GENE AND RELATED METHODS

[75] Inventors: Geraldine G. Miller, Franklin; Richard M. Peek, Jr., Nashville; Stuart A. Thompson, Whites Creek; Martin J. Blaser, Nashville, all of Tenn.

[73] Assignee: Vanderbilt University, Nashville, Tenn.

[21] Appl. No.: 650,528

[22] Filed: May 20, 1996

[51] Int. Cl.$^6$ ..................................................... C12N 15/00
[52] U.S. Cl. .......................... 435/172.2; 435/6; 435/172.1
[58] Field of Search .......................... 435/6, 172.1, 172.2

[56] References Cited

FOREIGN PATENT DOCUMENTS

WO 96/40893  12/1996  WIPO .

OTHER PUBLICATIONS

Peek, R.M. et al., Expression of iceA, a novel ulcer–associated H. pylori gene, is induced by contact with gastric epithelial cells and is associated with enhanced mucosal IL–, Gut, vol. 39 (supplement 2), Oct. 1996, A71, 3B:87.

Peek et al. "Expression of a Novel Ulcer–Associated *H. pylori* gene, ICEA Following Adherence to Gastric Epithelial Cells" Abstract A225, published Apr. 1996 for the Meetings of the American Gastroenterological Assoc. and American Assoc. for the Study of Liver Diseases held on May 19–22, 1996.

Peek et al. "Adherence–Induced Expression of a Novel *Helicobacter pylori* Gene and Correlation with Peptic Ulceration" Abstract 298, VIIIth Internat'l Workshop on Gastro–Duodenal Pathology and *Helicobacter pylori*, Edinburgh, Scotland Jul. 7–9, 1995.

Ghiara et al. "Role of the *H. pylori* Virulence Factors Vacuolating Cytotoxin, CagA, and Urease in a Mouse Model of Disease" *Infec. and Immun.* 63(10):4154–4160, Oct. 1995.

Hopkins, Robert and Morris, Jr., J. Glenn "*Helicobacter pylori*: The Missing Link in Perspective" *Am. J. Med.* 97:265–277, Sep. 1994.

Parsonnet et al. "*Helicobacter pylori* Infection and Gastric Lymphoma" *New Eng. J. Med.* 330(18):1267–1271, May 5, 1994.

Wong, K. K. and McClelland, Michael "Stree–Inducible Gene of *Salmonella typhimurium* Identified by Arbitrarily Primed PCR of RNA" *Proc. Natl. Acad. Sci. USA* 91:639–643, Jan. 1994.

Liang, P. and Pardee, Arthur B. "Differential Display of Eukaryotic Messenger RNA by Means of the Polymerase Chain Reaction" *Science* 257:967–971, Aug. 14, 1992.

Mekalanos, John J. "Environmental Signals Controlling Expression of Virulence Determinants in Bacteria" *J. Bacteriolog.* 174(1):1–7, Jan. 1992.

Crabtree et al. "Expression of 120 Kilodalton Protein and Cytotoxicity in *H. pylori*" *J. Clin. Pathol.* 45:733–734, 1992.

Akopyanz et al. "DNA Diversity Among Clinical Isolates of *H. pylori* Detected by PCR–Based RAPD Fingerprinting" *Nucl. Acids Res.* 20(19):5137–5142, 1992.

Nomura et al. "*Helicobacter pylori* Infection and Gastric Carcinoma Among Japanese Americans in Hawaii" *New Eng. J. Med.* 325:1132–1136, Oct. 17, 1991.

Crabtree et al. "Mucosal IgA Recognition of *H. pylori* 120kDa Protein, Peptic Ulceration, and Gastric Pathology" *Lancet* 338:332–335, Aug. 10, 1991.

Peterson, Walter L. "*Helicobacter pylori* and Peptic Ulcer Disease" *New Eng. J. Med.* 324(15):1043–1048, Apr. 11, 1991.

Cover et al. "Characterization of and Human Serlogic Response to Proteins in *Helicobacter pylori* Broth Culture Supernatants with Vacuolizing Cytotoxin Activity" *Infec. and Immun.* 58(3):603–610, Mar. 1990.

Dooley et al. "Prevalence of *Helicobacter pylori* Infection and Histologic Gastritis in Asymptomatic Persons" *New Eng. J. of Med.* 321:1562–1566, Dec. 7, 1989.

Figura et al. "Cytotoxin Production by *Campylobacter pylori* Strains Isolated from Patients with Peptic Ulcers and from Patients with Chronic Gastritis Only" *J. Clin. Microbiol.* 27(1):225–226, Jan. 1989.

Leunk et al. "Cytotoxic Activity in Broth–Culture Filtrates of *Campylobacter pylori* " *J. Med. Microbiol.* 26:93–99, 1988.

*Primary Examiner*—James C. Housel
*Assistant Examiner*—Ginny Allen Portner
*Attorney, Agent, or Firm*—Needle & Rosenberg, P.C.

[57] ABSTRACT

A purified IceA protein of *Helicobacter pylori* is provided. The protein is expressed as either an IceA 1 or an IceA 2 variant. A purified polypeptide fragment of the IceA protein is also provided. An antigenic fragment of IceA is provided. An isolated nucleic acid that encodes an IceA protein of *H. pylori* is provided. A nucleic acid that encodes an IceA 1 variant and a nucleic acid that encodes an IceA 2 variant is also provided. Fragments of the iceA gene are provided. A method of detecting the presence of an antibody against *H. pylori* in a sample is provided. The method comprises the following steps: a) contacting the sample with a purified IceA protein of *H. pylori* or a *H. pylori*-specific fragment thereof; and b) detecting the binding of the antibody in the sample to the protein or fragment, the detection of binding indicating the presence in the sample of antibodies against *H. pylori*. A method of detecting the presence of an antibody against an ulcerative *Helicobacter pylori* strain in a sample is also provided.

17 Claims, 7 Drawing Sheets

```
         G  A  I  C  V  G  D  D  V  K  I  G  A  N  A  V  V
A   1  GGGTGCGATTTGCGTGGGCGATGATGTGAAGATTGGGGCTAATGCGGTGG    50
       ||||||||||||||||||||||||||||||||||| || ||||||||||||
B   1  GGGTGCGATTTGCGTGGGCGATGATGTGAAGATCGGAGCTAATGCGGTGG    50
         G  A  I  C  V  G  D  D  V  K  I  G  A  N  A  V  V

L  S  D  L  P  T  G  S  T  A  V  G  T  K  A  K
   51  TGCTTTCAGATTTACCCACAGGTTCTACGGCTGTAGGCACTAAAGCTAAA   100
       |||||||||||||| ||||| |||||||||||||||||| ||||||||||
   51  TGCTTTCAGATTTGCCCACGGGTTCTACGGCTGTAGGCTCTAAAGCTAAA   100
       L  S  D  L  P  T  G  S  T  A  V  G  S  K  A  K

T  I  T  K  D  R  *
  101  ACCATCACAAAGGATCGTTAATTCTAGACAAGCGGTTGGAGT TTGCGC CA  150
       |||||||||| |||| ||||||| ||||||||| |||||||| |||||| ||
  101  ACCATCACAAAAGATCATTAATTTTAGACAAGCAGCTGGAGTTTGCGCCA   150
       T  I  T  K  D  H  *

151  TGCGGGTTAT TTTGAGG TAAATT GATTAGAATT TTTTAT AGAGAGATTTT   200
       |||||||| ||||||| || | ||| || || |||| ||||||
  151  TGCGGGTTGTTTTGAGAGTAAATTGATTTAATGTTATAGAGGGATTTT     200

201  TTAAAATGAGTAAAAGT...AAAAAAGAATTATTT TTGGAA CTCGCACAA   247
       |||       |||       |   |  ||||||| |   |     ||
  201  ATGAGAGTTAAGCGAGTTTGTTATTAAGCTATTTTTTAGGGATTTTGCGA   250

248  CCTGAT AAAAAT GGGGTGAGTCGTTGGGTAAGCGTTACAGAATTTTTAGG   297
       |   ||| ||   ||  |   || |||| |   |   |||
  251  TCAAATACTTAAATACTCAAATTAGGTTTATTTGTTAGTTAGACTATAGA   300

298  AAAATACCAAGGATTACAGCTAGGTAATGGGGGAGTTGGTGCAGGAATAG   347
       |   |  ||   |   |  ||| ||      |||    |    |   ||
  301  CTAGACTGGTAGTTTGGCGTTGGGT.ATATCACAATTTATATTTTAGGAG   349
                                  M  A  K  E  F  N  L  E  F  D  K  G  Q  T  L
  348  CTCAGCTTTGGCTAAAGAATTTAATTTGGAGTTTGATAAAGGGCAAACTC   397
       |    ||||   |   ||||||  ||     ||  ||| ||
  350  ATTTATAATGGCGGTTGTAATTAAAGTCGTTAATGGCAAAATACAGGAAT   399
                   M  A  V  V  I  K  V  V  N  G  K  I  Q  E  Y
```

FIG.2A

```
               G  N  S  I  D  R  I  R  L  N  G  Y  N  T  E  C
398  TAGGAAATTCTATTGATAGAATACGCTTGAATGGCTATAATACCGAATGT  447
     |  |||  ||    |||  ||  |   |   |  |  |||      |
400  ATGAGAATGGTAACTATAAAAGAACTTATGGTAGTAATATCGTAGCTGCA  449
        E  N  G  N  Y  K  R  T  Y  G  S  N  I  V  A  A
            V  F  N  Q  S  I  C  Q  D  I  K  N  H  Y  K  Q  Q
448  GTTTTTAACCAAAGTATCTGTCAAGACATTAAAAACCACTATAAGCAACA  497
     |  |  |      |||  |    |||     |     |||
450  GATACTGATGGGCATATTGTTGCTGCTGTTACTGCAAAGAGTAAAGTGGA  499
        D  T  D  G  H  I  V  A  A  V  T  A  K  S  V  E
         C  C  A  M  C  G  V  R  G  N  S  E  N  T  Q  I  E
498  ATGTTGCGCGATGTGTGGTGTGCGTGGCAACTCTGAAAACACTCAAATAG  547
       |    |   ||  ||  |          |   |||  ||   ||
500  AGAATATAAGAATGGTATT..........CATAAAAGAACCTACTAGAA  538
        E  Y  K  N  G  I           H  K  R  T  Y  *
        V  D  H  K  D  G  R  K  D  D  S  R  V  S  D  L
548  AAGTGGATCATAAAGACGGCCGCAAGGATGATTCAAGAGTTTCTGATTTA  597
     ||  |||  |||  |||     ||   |||     |  ||      | |
539  AATAGGGTAATAGCGACAAAAGCTTTGATACATTCAGCTAGTGGG.....  583
        N  T  Q  T  F  D  D  F  Q  A  L  C  K     A  C  N
598  AACACACAGACTTTTGATGATTTTCAGGCTTTATGCAAA..GCTTGTAAC  645
      |  |||  ||  ||||  |||  |||   ||       ||  |
584  .......GGGGTGTTGCTGTTTTTTTGGCAGTATTTTAATGAGCAGTTGC  626

D  K  K  R  Q  I  C  K  K  C  K  E  S  G  Y  R  F
646  GATAAGAAACGCCAGATTTGTAAAAAATGCAAAGAAAGTGGCTATAGATT  695
     ||||  |||  ||    |||  ||  |           ||||
627  GATAGAAAAAGTCTTTATTGGCAATAGGGGGGGTTGTCTCGTTGTTTTAA  676

D  A  T  K  I  P  G  N  Y  Y  S  F  Y  E  G  E  A
696  TGACGCAACAAAAATTCCTGGCAATTATTATTCTTTCTATGAGGGGGAGG  745
     |||  ||    |   |   ||  ||    |          |   |   |
677  TGAAGCGATTGGTAGGGCGTGCGGTGTTAAAAAACGATCATCGTTTCACA  726

E  Y  D  G  C  V  G  C  Y  Q  Y  D  P  I  Q  Y
746  CTGAATATGATGGTTGTGTGGGCTGTTATCAATATGACCCCATACAATAC  795
     |||   |  ||||  |       ||||   ||        |  |||  ||
727  TAGGATTGATTAGTTGGTTTTAAGATTATTTTAATCGTGGGGTTTAAGAC  776
```

FIG.2B

```
        R   K   T   C   N   D   R   I   Y   N   E   G   Y   Q   K   G   Y
796  AGGAAAACTTGTAATGATAGGATATACAATGAAGGGTATCAAAAAGGCTA            845
              || | |||   |   |   |   |    ||   ||||       |
777  ..........TTATTCATAATCAAGTTATGTTACAATACATAAAATTTAA            816

G   D   G   Y   Q   I   G   Y   H   Q   K   T   T   L   *
846  TGGTGATGGGTATCAAATTGGATACCATCAAAAAACTACTTTATAGCGGT            895
      |  |  ||      || |||         |   ||||    |   |  |
817  TTTTAATAATAGCCATATT.....TATTTTAAAGAAGCATACAAACACAG            861

M   N   Y   I   G   S   K   Y   K   L   I   P   F   I   K   E
896  TGCAATGAACTACATCGGCTCTAAATACAAGCTCATTCCCTTTATTAAAG            945
     ||||||||||||||||||||||||||||||||||||||||||||||||| |
862  ATCAATGAACTACATCGGCTCTAAATACAAGCTCATTCCCTTTATTAAGG            911
        M   N   Y   I   G   S   K   Y   K   L   I   P   F   I   K   E

N   I   H   A   V   V   G   H   D
946  AAAATATCCATGCGGTTGTAGGCCATGATC       975
     |||||||||||||||||||||||||||||
912  AAAATATCCATGCGGTTGTAGGCCATGATC       941
        N   I   H   A   V   V   G   H   D
```

FIG.2C

ICEA GENE AND RELATED METHODS

ICEA GENE AND RELATED METHODS

This work was supported by NIH R01 HL53771, R01 DK50837, T-32DK07673-02, and by the Medical Research Service of the Department of Veterans Affairs. The government has certain rights in the invention.

BACKGROUND OF THE INVENTION

1. Field of the Invention

The invention pertains to the iceA gene of *Helicobacter pylori* and to the antigenic polypeptides encoded by the genes, as well as methods of using the gene and polypeptides to diagnose *H. pylori* infection and predisposition to peptic ulceration and other diseases associated with *H. pylori* infection.

2. Background Art

*Helicobacter pylori* infection causes chronic superficial gastritis (1), and may lead to duodenal and gastric ulcer disease, gastric adenocarcinoma, or non-Hodgkins lymphoma of the stomach (2–4). However, most infected persons remain asymptomatic, with only 10–20% of infected persons developing one of these illnesses (5). One putative virulence factor elaborated by 40–60% of *H. pylori* isolates is a toxin, encoded by vacA, that induces vacuolation of eukaryotic cells and injury to gastric epithelium (6,7). Another strain-specific *H. pylori* constituent is the 120–132 kDa cytotoxin-associated gene A (cagA) product which is present in 60% of strains (8,9). Although cagA genotype and cytotoxin expression both are associated with peptic ulcer disease (8,10,11), the majority of persons infected with such strains do not progress to ulceration, suggesting that other *H. pylori* genes also are important in disease pathogenesis.

The extensive genomic diversity that exists among *H. pylori* isolates (12) hinders identification of putative strain-specific virulence determinants. Another factor that may limit detection of genes relevant to pathogenesis is that bacterial transcripts expressed during growth in vitro may not reflect in vivo expression (13). Because so little is known about the pathogenesis of *H. pylori*, there is a need to identify genes expressed selectively in ulcer-causing strains.

The present invention meets this need by demonstrating that adherence to gastric epithelial cells induces the selective expression of a novel *H. pylori* gene, iceA (induced by contact with epithelium), that is highly correlated with peptic ulcer disease. iceA exists in two major allelic variants which are not associated with previously described *H. pylori* virulence determinants.

Previous methods used to identify genes that are selectively expressed under specific environmental conditions have relied largely on subtractive hybridization techniques (35). In contrast, the current experiments demonstrate that RAP RT-PCR is an effective approach for the identification of a conditionally expressed gene in *H. pylori*. The current method provide a means by which induction of prokaryotic virulence genes by be identified following stimulation with factors that actually reflect in vivo pathogenesis. Having shown this, the use of RAP RT-PCR therefore could be extended to other bacteria to identify up-regulation of undescribed genes that may reflect pathogenetic mechanisms.

SUMMARY OF THE INVENTION

A purified IceA protein of *Helicobacter pylori* is provided. The protein is expressed as either an IceA 1 or an IceA 2 variant. A purified polypeptide fragment of the IceA protein is also provided. An antigenic fragment of IceA is provided.

An isolated nucleic acid that encodes an IceA protein of *H. pylori* is provided. A nucleic acid that encodes an IceA 1 variant, termed an iceA 1 allele, is provided. A nucleic acid that encodes an IceA 2 variant, termed an iceA 2 allele, is also provided. Fragments of the iceA gene are provided.

A method of detecting the presence of an antibody against *H. pylori* in a sample is provided. The method comprises the following steps: a) contacting the sample with a purified IceA protein of *H. pylori* or a *H. pylori*-specific fragment thereof; and b) detecting the binding of the antibody in the sample to the protein or fragment, the detection of binding indicating the presence in the sample of antibodies against *H. pylori*. The presence of the antibodies against *H. pylori* is correlated with current or previous infection with *H. pylori* in the subject from whom the sample is obtained.

A method of detecting the presence of an antibody against an ulcerative *Helicobacter pylori* strain in a sample is also provided. The method comprises the following steps: a) contacting the sample with a purified IceA protein from an ulcerative *Helicobacter pylori* strain or an ulcerative *Helicobacter pylori* strain-specific fragment thereof; and b) detecting the binding of the antibody in the sample to the protein or fragment, the detection of binding indicating the presence in the sample of antibodies against an ulcerative *Helicobacter pylori* strain. The presence of the antibodies against an ulcerative *Helicobacter pylori* strain is correlated with current or previous infection with an ulcerative *H. pylori* strain in the subject from whom the sample is obtained. Thus, differential diagnosis of infection with ulcerative versus non-ulcerative strains of *H. pylori* is permitted.

BRIEF DESCRIPTION OF THE FIGURES

FIGS. 2A, 2B and 2C shows the nucleotide and deduced amino acid sequences of pRMP100 from a genomic library of 60190 and alignment of regions corresponding to cysE, iceA and M. Hpyl in *H. pylori* strains 60190 (A) and J178 (B). Potential ribosome binding sites (RBS) are overlined and putative promoter elements are boxed |−35 sequences in bold boxes, −10 sequences in standard boxes|. The primers (ser-1, meth-3) used to amplify the iceA region from clinical strains are underlined at positions 1–23 (5'-3') and 975–952 (5'-3') of 60190 sequence, respectively. The primers (178–1, 178–2) used for PCR amplification to classify iceA alleles from 40 clinical strains are underlined at positions 659–680 (5'-3') and 776–756 (5'-3') of J178 sequence, respectively.

Figure 1A:
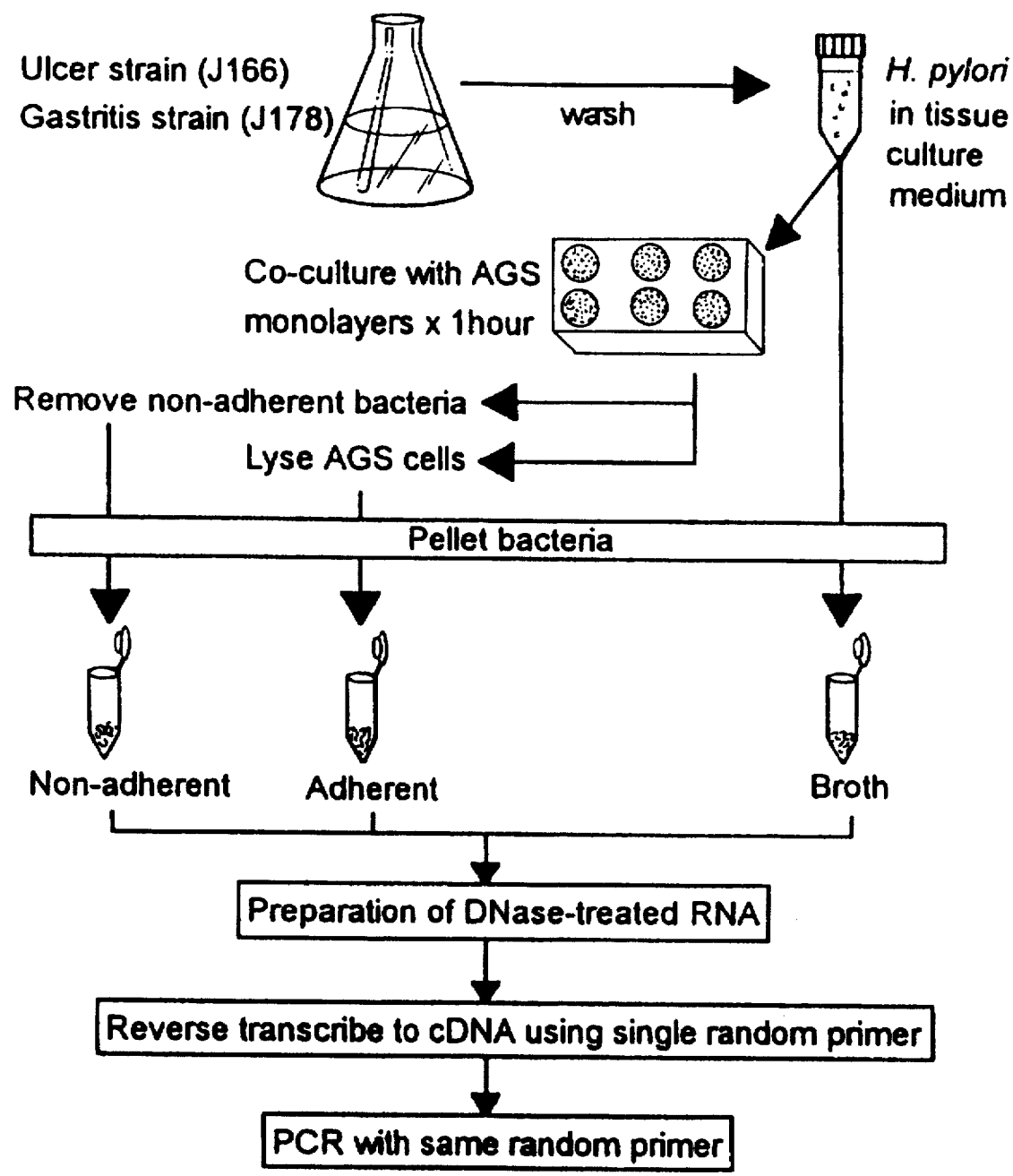
FIG. 1A depicts the preparation of RAP RT-PCR templates as described in the Examples. RAP RT-PCR identifies a strain-specific product induced by adherence to AGS cells.

DETAILED DESCRIPTION
IceA Protein and Fragments

A purified IceA protein of *Helicobacter pylori* is provided. The protein is expressed as either an IceA 1 variant (also referred to as "IceA 1") or an IceA 2 variant (also referred to as "IceA 2"). The IceA protein can be defined by any one or more of the typically used parameters. Examples of these parameters include, but are not limited to molecular weight (calculated or empirically determined), isoelectric focusing point, specific epitope(s), complete amino acid sequence, sequence of a specific region (e.g., N-terminus) of the amino acid sequence. The IceA protein can be encoded by any coding sequence, including those provided herein.

The IceA 1 variant has two isoforms, an approximately 21 kDa calculated molecular weight isoform, and an approximately 15 kDa calculated molecular weight isoform. Both isoforms of the IceA 1 variant are encoded by a single open reading frame (ORF) having two alternative start codons. The IceA 1 variant can be defined by its variant-specific N-terminal sequence. For example, the variant-specific N-terminal sequence can be the amino acid sequence encoded, for example, by nucleotides 25–81 of SEQ ID NO:1. Examples of IceA 1 variants and coding sequences are shown in SEQ ID Nos:1–5, 63 and 101. SEQ ID NO:5 shows a partial sequence of of an IceA 1-encoding nucleic acid.

The IceA 2 variant has an approximately 7 kDa calculated molecular weight. The IceA 2 variant can be defined by its variant-specific N-terminal sequence. For example, the variant-specific N-terminal sequence can be amino acid sequences encoded, for example, by nucleotides 163–195 of SEQ ID NO:6. Examples of IceA 2 variants are shown in SEQ ID Nos:6–10. SEQ ID NO:10 shows a partial sequence of an IceA 2-encoding nucleic acid.

As used herein, "purified" refers to a protein (polypeptide, peptide, etc.) that is sufficiently free of contaminants or cell components with which it normally occurs to distinguish it from the contaminants or other components of its natural environment. The purified protein need not be homogeneous, but must be sufficiently free of contaminants to be useful in a clinical or research setting, for example, in an assay for detecting antibodies to the protein.

Having provided an example of a purified IceA protein, the invention also enables the purification of IceA homologs from other *H. pylori* strains. For example, an antibody raised against the exemplary protein can be used routinely to screen preparations of other *H. pylori* strains for homologous proteins that react with the IceA-specific antibody. An IceA protein having the N-terminal sequence of amino acids encoded by nucleotides 25–81 of SEQ ID NO:1 or amino acids encoded by nucleotides 163–195 of SEQ ID NO:6, can be routinely identified in and obtained from other organisms using the methods taught herein and others known in the art. For example, the conserved DNA encoding a conserved amino acid sequence can be used to probe genomic DNA or DNA libraries of an organism to predictably obtain the iceA gene for that organism. The gene can then be cloned and expressed as the IceA protein, and purified according to any of a number of routine, predictable methods. An example of the routine protein purification methods available in the art can be found in Pei et al. (45).

An example of an IceA protein of *H. pylori* having the amino acid sequence defined in the Sequence Listing as SEQ ID NO:2 is provided. This is the amino acid sequence for an IceA 1 variant from strain 60190 (ATCC Accession No. 49503), a reference strain that causes ulcer disease.

An example of an IceA protein of *H. pylori* having the amino acid sequence defined in the Sequence Listing as SEQ ID NO:101 is provided. This is the amino acid sequence for an IceA 1 variant of strain J166, a clinical isolate that causes ulcer disease.

An example of an IceA protein of *H. pylori* having the amino acid sequence encoded by the nucleotide sequence defined in the Sequence Listing as SEQ ID NO:3 is provided. This is the amino acid sequence for an IceA 1 variant of strain A101, a clinical isolate that causes ulcer disease. The nucleotide sequence of this iceA 1 variant has not been verified on both sequences.

An example of an IceA protein of *H. pylori* having the amino acid sequence encoded by the nucleotide sequence defined in the Sequence Listing as SEQ ID NO:5 is provided. This is the amino acid sequence for an IceA 1 variant of strain J128, a clinical isolate that causes ulcer disease. The nucleotide sequence of this iceA 1 variant has not been verified on both sequences.

An example of an IceA protein of *H. pylori* having the amino acid sequence defined in the Sequence Listing as SEQ ID NO:7 is provided. This is the amino acid sequence for an IceA 2 variant expressed by strain J178, which causes gastritis, but not ulceration.

An example of an IceA protein of *H. pylori* having the amino acid sequence encoded by the nucleotide sequence defined in the Sequence Listing as SEQ ID NO:8 is provided. This is the amino acid sequence for an IceA 2 variant expressed by strain J174, which causes gastritis, but not ulceration. The nucleotide sequence of this iceA 2 variant has not been verified on both sequences.

An example of an IceA protein of *H. pylori* having the amino acid sequence encoded by the nucleotide sequence defined in the Sequence Listing as SEQ ID NO:9 is provided. This is the amino acid sequence for an IceA 2 variant expressed by strain J195, which causes gastritis, but not ulceration. The nucleotide sequence of this iceA 2 variant has not been verified on both sequences.

An example of an IceA protein of *H. pylori* having the amino acid sequence encoded by the nucleotide sequence defined in the Sequence Listing as SEQ ID NO:10 is provided. This is the amino acid sequence for an IceA 2 variant expressed by strain J262, which causes gastritis, but not ulceration. The nucleotide sequence of this iceA 2 variant has not been verified on both sequences.

The *H. pylori* IceA protein can comprise a sequence of amino acids selected from the group consisting of the sequences defined in the Sequence Listing as SEQ ID Nos:64–100. These SEQ ID NOS give amino acid sequences for a variant-specific conserved region of the 60190 strain of *H. pylori*, which produces IceA variant 1. The proteins comprising these specific sequences will by definition be IceA 1. The methods used to select these conserved specific regions of IceA 1 are routine and can be used to identify other IceA 1 variants from other sources.

The *H. pylori* IceA protein can comprise a sequence of amino acids that are selected from the group consisting of the polypeptides and peptides encoded sequences defined in the Sequence Listing as SEQ ID NOS:6 and 8–10 that are for specific, conserved region(s) of the J178-like strains of *H. pylori*, which express the IceA variant 2. These proteins will by definition be IceA 2 proteins. The methods used to select conserved specific regions of IceA 2 are routine and can be used to identify other IceA 2 variants from other sources.

A purified polypeptide fragment of the IceA protein is also provided. The term "fragment" as used herein regarding IceA, means a molecule of at least 5 contiguous amino acids of IceA that has at least one function shared by IceA or a region thereof. These functions can include antigenicity; epithelial cell binding; DNA binding (as in transcription factors); RNA binding (as in regulating RNA stability or degradation, thereby affecting the half-life of specific mRNAs and the amount of protein that can be translated from them); protease activity or proteolysis; and toxin activity. The IceA fragment can be specific for *Helicobacter pylori*. As used herein to describe an amino acid sequence (protein, polypeptide, peptide, etc.), "specific" means that the amino acid sequence is not found identically in any other source. The determination of specificity is made routine, because of the availability of computerized amino acid sequence databases, wherein an amino acid sequence of almost any length can be quickly and reliably checked for the existence of identical sequences. If an identical sequence is not found, the protein is "specific" for the recited source. An IceA fragment can be protein specific (i.e., found in IceA from any source, but not in other proteins), species-specific (e.g., found in the IceA of *H. pylori*, but not of other species), or variant-specific (i.e., found in an IceA 1 variant, but not in an IceA 2 variant).

An antigenic fragment of IceA is provided. The IceA fragment can be from an IceA from any source. An antigenic fragment has an amino acid sequence of at least about 5 consecutive amino acids of an IceA amino acid sequence and binds an antibody. An antigenic fragment can be selected by applying the routine technique of epitope mapping to IceA to determine the regions of the proteins that contain epitopes reactive with serum antibodies or are capable of eliciting an immune response in an animal. Once the epitope is selected, an antigenic polypeptide containing the epitope can be synthesized directly, or produced recombinantly by cloning nucleic acids encoding the polypeptide in an expression system, according to the standard methods. Alternatively, an antigenic fragment of the antigen can be isolated from the whole antigen or a larger fragment by chemical or mechanical disruption. Fragments can also be randomly chosen from a known IceA sequence and synthesized. The purified fragments thus obtained can be tested to determine their antigenicity and specificity by routine methods.

An *H. pylori*-specific IceA fragment having an amino acid sequence selected from the group consisting of the unique sequences defined in the Sequence Listing as SEQ ID NO:2, SEQ ID NO:7 and SEQ ID NO:101 and specific fragments thereof is also provided.

Modifications to any of the above proteins or fragments can be made, while preserving the specificity and activity (function) of the native protein or fragment thereof. As used herein, "native" describes a protein that occurs in nature.

The modifications contemplated herein can be conservative amino acid substitutions, for example, the substitution of a basic amino acid for a different basic amino acid. Modifications can also include creation of fusion proteins with epitope tags or known recombinant proteins or genes encoding them created by subcloning into commercial or non-commercial vectors (e.g., polyhistidine tags, flag tags, myc tag, glutathione-S-transferase |GST| fusion protein, xylE fusion reporter construct). Furthermore, the modifications contemplated will not affect the function of the protein or the way the protein accomplishes that function (e.g., its secondary structure or the ultimate result of the protein's activity. These products are equivalent to IceA. The means for determining these parameters are well known.

Having provided the novel pathogenesis-associated IceA protein, a method of using it as a toxin is also provided. Particularly, the protein can be administered directly to a tumor (e.g., gastric carcinoma) or population of cells (e.g., T cells), or it can be expressed in the tumor or other cell after delivery of an iceA sequence encoding the protein or an active fragment. The tumor cell or other cell can, thus, be killed when the IceA protein or fragment is expressed.

Determining Immunogenicity

The purified antigenic polypeptides can be tested to determine their immunogenicity and specificity. Briefly, various concentrations of a putative immunogenic specific fragment are prepared and administered to an animal and the immunological response (e.g., the production of antibodies or cell mediated immunity) of an animal to each concentration is determined. The amounts of antigen administered depend on the subject, e.g. a human, a guinea pig, or a gnotobiotic piglet, the condition of the subject, the size of the subject, etc. Thereafter an animal so inoculated with the antigen can be exposed to the bacterium to determine the vaccine effect of the specific antigenic fragment. The specificity of the fragment can be ascertained by testing sera, other fluids or lymphocytes from the inoculated animal for cross reactivity with other closely related bacteria.

Nucleic Acids Encoding IceA

An isolated nucleic acid that encodes an IceA protein of *H. pylori* is provided. As used herein, the term "isolated" means a nucleic acid is separated from at least some of other components of the naturally occurring organism, for example, the cell structural components and/or other genes. The isolation of the nucleic acids can therefore be accomplished by techniques such as cell lysis followed by phenol plus chloroform extraction, followed by ethanol precipitation of the nucleic acids (20). It is not contemplated that the isolated nucleic acids are necessarily totally free of non-nucleic acid components, but that the isolated nucleic acids are isolated to a degree of purification to be useful in a clinical, diagnostic, experimental, or other procedure such as gel electrophoresis, Southern or dot blot hybridization, or PCR. A skilled artisan in the field will readily appreciate that there are a multitude of procedures which may be used to isolate the nucleic acids prior to their use in other procedures. These include, but are not limited to, lysis of the cell followed by gel filtration or anion exchange chromatography, binding DNA to silica in the form of glass beads, filters or diatoms in the presence of high concentration of chaotropic salts, or ethanol precipitation of the nucleic acids.

The nucleic acids of the present invention can include positive and negative strand RNA as well as DNA and is meant to include genomic and subgenomic nucleic acids found in the naturally occurring organism. The nucleic acids contemplated by the present invention include double stranded and single stranded DNA of the genome, complementary positive stranded CRNA and mRNA, and complementary CDNA produced therefrom and any nucleic acid which can selectively or specifically hybridize to the isolated nucleic acids provided herein.

An isolated nucleic acid that encodes an IceA protein of *H. pylori* is species-specific (i.e., does not encode the IceA of other species and does not occur in other species). The nucleic acid can also be variant-specific (i.e., encodes an IceA 1 variant, but not in an IceA 2 variant). Examples of the nucleic acids contemplated herein include the nucleic acids that encode each of the IceA proteins or fragments thereof described herein.

A nucleic acid that encodes an IceA 1 variant is termed an iceA 1 allele. Examples of iceA 1 alleles are provided in the Sequence Listing as SEQ ID NOS:1,3–5 and 63. SEQ ID NO:5 is a partial sequence. Examples of nucleic acids encoding the IceA 1 variant-specific N-terminal sequences can be nucleotides 25–81 of SEQ ID NO:1. Other examples of iceA 1 allele-specific nucleic acids are shown in SEQ ID NOS:11–48. Any other allele-specific fragments can be routinely obtained and their structure (sequence) determined by routine means.

A nucleic acid that encodes an IceA 2 variant is termed an iceA 2 allele. Examples of iceA 2 alleles are provided in the Sequence Listing as SEQ ID NOS:6 and 8–10 Sequence ID NO:11 is a partial sequence. Examples of variant-specific nucleic acids can be nucleotides 163–195 of SEQ ID NO:6. Other examples of iceA 2 allele-specific nucleic acids are shown in SEQ ID NOS:49–62. Any other iceA 2 allele-specific fragments can be routinely determined using the same methods as used herein.

Sequence variability among iceA 1 alleles ranged from about 88% identity down to about 73% identity. That is, for the alleles sequenced, the most divergent share about 73% nucleotide identity. The closest iceA 2 allele shares only about 44% identity with 60190 iceA 1. Among the iceA 2 alleles, the most divergent sequences share about 78% identity.

The iceA gene can be distinguished from other nucleic acids, because of its conserved genomic location. Particularly, iceA is flanked upstream by a sequence having strong homology to a serine methyltransferase (cysE) of *Bacillus stearothermophilus*, and downstream by an ORF having strong homology to a DNA adenine methyltransferase in *Neisseria lactamica* (M. NlaIII) designated *M.Hypl*. In all of the strains tested so far iceA is flanked by cysE and *M.Hpyl*. This conserved location also makes obtaining iceA from other sources in which it occurs both routine and predictable. For example, as shown below, primers that hybridize with the highly conserved cysE and *M.Hypl*. can be used to amplify iceA from any sample in which it occurs.

IceA-encoding nucleic acids can be isolated from an organism in which it is normally found (e.g., *H. pylori*), using any of the routine techniques. For example, a genomic DNA or cDNA library can be constructed and screened for the presence of the nucleic acid of interest using one of the present iceA nucleic acids as a probe. Methods of constructing and screening such libraries are well known in the art and kits for performing the construction and screening steps are commercially available (for example, Stratagene Cloning Systems, La Jolla, Calif.). Once isolated, the nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al. (20).

IceA-encoding nucleic acids can also be synthesized. For example, a method of obtaining a DNA molecule encoding a specific IceA is to synthesize a recombinant DNA molecule which encodes the IceA. For example, oligonucleotide synthesis procedures are routine in the art and oligonucleotides coding for a particular protein region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. For example, Cunningham, et al. (38), have constructed a synthetic gene encoding the human growth hormone by first constructing overlapping and complementary synthetic oligonucleotides and ligating these fragments together. See also, Ferretti, et al. (39), wherein synthesis of a 1057 base pair synthetic bovine rhodopsin gene from synthetic oligonucleotides is disclosed. By constructing an iceA in this manner, one skilled in the art can readily obtain any particular iceA with modifications at any particular position or positions. See also, U.S. Pat. No. 5,503,995 which describes an enzyme template reaction method of making synthetic genes. Techniques such as this are routine in the art and are well documented. DNA encoding IceA or IceA fragments can then be expressed in vivo or in vitro.

Once a nucleic acid encoding a particular IceA of interest, or a region of that nucleic acid, is constructed, modified, or isolated, that nucleic acid can then be cloned into an appropriate vector, which can direct the in vivo or in vitro synthesis of that wild-type and/or modified IceA. The vector is contemplated to have the necessary functional elements that direct and regulate transcription of the inserted gene, or hybrid gene. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al. (20)). Thus, the iceA or iceA fragment can be in a vector and the vector can be in a host for expressing the nucleic acid.

Having provided and taught how to obtain a nucleic acid that encodes IceA, an isolated nucleic acid that encodes a fragment of IceA is also provided. The fragment can be obtained using any of the methods applicable to the full gene. The fragment can encode a protein specific fragment (i.e., found in IceA, but not in other proteins), a species-specific fragment (e.g., found in the IceA of *H. pylori*, but not in the IceA of other species), or a variant-specific fragment (i.e., found in one variant, but not in the other variant). Nucleic acids encoding protein-specific, species-specific or variant-specific fragments of IceA are themselves gene-specific, species-specific or allele-specific fragments of the iceA gene.

Examples of fragments of an iceA gene are provided in SEQ ID NOS:11–62. Fragments specific for the iceA 1 allele are provided in SEQ ID NOS:11–48. Fragments specific for the iceA 2 allele are provided in SEQ ID NOS:49–62. These examples of fragments are in no way limiting. The same routine computer analyses used to select these examples of fragments can be routinely used to obtain others. iceA gene fragments can be primers for PCR or probes, which can be species-specific, gene-specific or allele-specific. iceA fragments can encode antigenic or immunogenic fragments of IceA that can be used in diagnostic methods or as a vaccine component. iceA fragments can encode fragments of IceA having DNA binding, RNA binding, transcription activation, proteolysis, etc. as described above, or in other uses that may become apparent.

An isolated nucleic acid of at least 10 nucleotides that specifically hybridizes with the nucleic acid of any SEQ ID NOS:1,3,4,5,6,8–10 and 63 under selected conditions is provided. For example, the conditions can be polymerase chain reaction conditions and the hybridizing nucleic acid can be primer consisting of a specific fragment of the reference sequence or a nearly identical nucleic acid that hybridizes only to the exemplified iceA gene or a *H. pylori* homolog thereof.

The invention provides an isolated nucleic acid that specifically hybridizes with the iceA gene shown in the sequence set forth as SEQ ID Nos:1,3,4,5,6 and 63 under the conditions of about 16 hrs at about 65° C., about 5× SSC, about 0.1% SDS, about 2× Denhardt's solution, about 150 µg/ml salmon sperm DNA with washing at about 65° C., 30 min, 2×, in about 0.1× SSPE/0.1% SDS. Alternative hybridization conditions include 68° C. for about 16 hours in buffer containing about 6× SSC, 0.5% sodium dodecyl sulfate, about 5× Denhardt's solution and about 100 µg salmon sperm DNA, with washing at about 60° C. in about 0.5× SSC (Tummuru, M. K. R., T. Cover, and M. J. Blaser (40). For example, the hybridizing nucleic acid can be a probe that hybridizes only to the exemplified IceA gene or a homolog thereof. Thus, the hybridizing nucleic acid can be a naturally occurring homolog of the exemplified IceA genes. The hybridizing nucleic acid can also include insubstantial base substitutions that do not prevent hybridization under the stated conditions or affect the function of the encoded protein, the way the protein accomplishes that function (e.g., its secondary structure or the ultimate result of the protein's activity. The means for determining these parameters are well known.

As used herein to describe nucleic acids, the term "selectively hybridizes" excludes the occasional randomly hybridizing nucleic acids as well as nucleic acids that encode other known homologs of the present proteins. The selectively hybridizing nucleic acids of the invention can have at least 70%, 73%, 78%, 80%, 85%, 88%, 90%, 91%, 92%, 93%, 94%, 95%, 96%, 97%, 98% and 99% complementarity with the segment and strand of the sequence to which it hybridizes. The nucleic acids can be at least 10, 18, 20, 25, 50, 100, 150, 200, 300, 500, 550, 750, 900, 950, or 1000 nucleotides in length, depending on whether the nucleic acid is to be used as a primer, probe or for protein expression. Thus, the nucleic acid can be an alternative coding sequence for the protein, or can be used as a probe or primer for detecting the presence *H. pylori* or obtaining iceA. If used as primers, the invention provides compositions including at least two nucleic acids which selectively hybridize with different regions so as to amplify a desired region. Depending on the length of the probe or primer, it can range between 70% complementary bases and full complementarity and still hybridize under stringent conditions. For example, for the purpose of diagnosing the presence of *H. pylori*, the degree of complementarity between the hybridizing nucleic acid (probe or primer) and the sequence to which it hybridizes (*H. pylori* DNA from a sample) should be at least enough to exclude hybridization with a nucleic acid from a related bacterium. The invention provides examples of these nucleic acids of *H. pylori*, so that the degree of complementarity required to distinguish selectively hybridizing from nonselectively hybridizing nucleic acids under stringent conditions can be clearly determined for each nucleic acid. It should also be clear that the hybridizing nucleic acids of the invention will not hybridize with nucleic acids encoding unrelated proteins (hybridization is selective) under stringent conditions.

"Stringent conditions" refers to the washing conditions used in a hybridization protocol. In general, the washing conditions should be a combination of temperature and salt concentration chosen so that the denaturation temperature is approximately 5°–20° C. below the calculated $T_m$ of the hybrid under study. The temperature and salt conditions are readily determined empirically in preliminary experiments in which samples of reference DNA immobilized on filters are hybridized to the probe or protein coding nucleic acid of interest and then washed under conditions of different stringencies. For example, the iceA PCR fragment described below is used as a specific radiolabeled probe for *H. pylori* iceA by performing hybridizations at 68° C. in the presence of 5× SSPE (12), then removing non-specific hybrids by high-stringency washes of O.1× SSPE at 68° C. as described in reference 12, chapter 9. Hybridizations with oligonucleotide probes shorter than 18 nucleotides in length are done at 5°–10° C. below the estimated $T_m$ in 6× SSPE, then washed at the same temperature in 2× SSPE as described in reference 12, chapter 11. The $T_m$ of such an oligonucleotide can be estimated by allowing 2° C. for each A or T nucleotide, and 4° C. for each G or C. An 18 nucleotide probe of 50% G+C would, therefore, have an approximate $T_m$ of 54° C.

Serological Methods of Diagnosing *H. pylori* Infection

A method of detecting the presence of an antibody against *H. pylori* in a sample is provided. The method comprises the following steps: a) contacting the sample with a purified IceA protein of *H. pylori* or a *H. pylori*-specific fragment thereof; and b) detecting the binding of the antibody in the sample to the protein or fragment, the detection of binding indicating the presence in the sample of antibodies against *H. pylori*. The presence of the antibodies against *H. pylori* is correlated with current or previous infection with *H. pylori* in the subject from whom the sample is obtained. As used herein, the term "antibody against *H. pylori*" means an antibody elicited in a subject by exposure to *H. pylori*.

A method of diagnosing *H. pylori* infection in a subject by detecting in a sample from the subject the presence of an *H. pylori*-specific antigen is also contemplated. The presence of the *H. pylori*-antigen is correlated with *H. pylori* infection in the subject from whom the sample is obtained. The antigen can be IceA or an antigenic fragment thereof.

The sample can be a fluid sample comprising any body fluid which would contain IceA, a *H. pylori* cell containing the antigen or an antibody against *H. pylori*, such as blood, plasma, serum, saliva, gastric juice, sputum, mucus, urine and stool. Tissue samples can include gastric or duodenal tissue.

The term "contacting" as used herein refers to the numerous contacting protocols and binding detection protocols are routinely practiced in the art. These include, but are not limited to the examples described below.

ELISA

Immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Competitive Inhibition Assay

Another immunologic technique that can be useful in the detection of *H. pylori* expressing IceA or previous *H. pylori* infection utilizes monoclonal antibodies (MAbs) for detection of antibodies specifically reactive with IceA antigen. Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

Micro-Agglutination Assay

A micro-agglutination test can also be used to detect the presence of the IceA-possessing *H. pylori* strain in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In a modification of the above test, antibodies specifically reactive with the antigen can be bound to the beads and antigen in the tissue or body fluid thereby detected.

Sandwich Assay/Flow Cytometry/Immunoprecipitation

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides IceA antigen for the detection of *H. pylori* or previous *H. pylori* infection, other serological methods such as flow cytometry and immunoprecipitation can also be used as detection methods.

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy), alkaline phosphatase (for biochemical detection by color change) and radioisotopes (for radiography). The detection methods and moieties used can be selected, for example, from the list above or other suitable examples by the standard criteria applied to such selections (46).

The above method using a purified IceA protein selected from the group consisting of the proteins defined in the Sequence Listing as SEQ ID NOS:2,7 and 101 specifically provided.

The above method using a fragment of IceA selected from the group consisting of the fragments defined in the Sequence Listing as SEQ ID NOS:64–100 is also provided.

A method of detecting the presence of an antibody against an ulcerative *Helicobacter pylori* strain in a sample is also provided. The method comprises the following steps: a) contacting the sample with a purified IceA protein from an ulcerative *Helicobacter pylori* strain or an ulcerative *Helicobacter pylori* strain-specific fragment thereof; and b) detecting the binding of the antibody in the sample to the protein or fragment, the detection of binding indicating the presence in the sample of antibodies against an ulcerative *Helicobacter pylori* strain. The presence of the antibodies against an ulcerative *Helicobacter pylori* strain is correlated with current or previous infection with an ulcerative *H. pylori* strain in the subject from whom the sample is obtained.

A method of detecting ulcerative strains of *H. Pylori*, wherein the purified IceA protein from an ulcerative *Helicobacter pylori* strain is selected from the group consisting of the proteins defined in the Sequence Listing as SEQ ID Nos:2 and 101 is specifically provided. These are examples of the IceA 1 variant. Others can be used as well.

A method of detecting the presence of an antibody against an ulcerative *Helicobacter pylori* strain in a sample using an IceA fragment selected from the group consisting of the fragments defined in the Sequence Listing as SEQ ID NO:64–100 is specifically provided. These are examples fragments of the IceA 1 variant.

Nucleic Acid Diagnosis of *H. pylori* Infection

A method of detecting *Helicobacter pylori* infection in a subject, comprising detecting the presence of a nucleic acid encoding IceA in a specimen from the subject, the presence of the nucleic acid indicating infection with *Helicobacter pylori*. A method is provided for detecting the presence of a *H. pylori*-specific nucleic acid in a sample, comprising detecting in the sample a nucleic acid specific for the iceA gene of *H. pylori* or an *H. pylori*-specific fragment thereof. The detection of the nucleic acid is correlated with the presence of *H. pylori* in the subject from whom the sample is obtained.

A method of detecting the presence of a *H. pylori*-specific nucleic acid in a sample, wherein the *H. pylori*-specific nucleic acid or *H. pylori*-specific fragment thereof is selected from the group consisting of nucleic acids defined in the Sequence Listing as SEQ ID NOS:1,3–6, and 8–63 is specifically provided.

Method of Predicting Predisposition to Gastric Carcinoma

The present invention also provides a method of determining predisposition to gastric carcinoma in a subject. The method can be accomplished according to the methods set forth herein for the detection of IceA 1 variant-specific *H. pylori* strains or for the detection of antibodies specific to IceA 1 variant. The presence of the antigens or specific antibodies indicates a predisposition of the subject to gastric carcinoma. The methods described herein for detecting nucleic acids specific for IceA-expressing strains can also be used.

Differential Expression of Virulence Associated Genes

A method of comparing gene expression in *H. pylori* strains having different clinical consequences is provided. The method comprises the steps of a) isolating RNA from the *Helicobacter pylori* strains, b) reverse transcribing RNA from the strains to cDNA using a random primer. c) amplifying the cDNA to produce amplification products and d) comparing the amplification products of one strain with the amplification products of another strain, the amplification products of a strain being correlated with gene expression in the strain.

The method of comparing gene expression in *H. pylori* strains having different clinical consequences, further comprising the step of providing a selected stimulus to the strains being compared prior to the RNA isolation step is also provided. When the strains being compared are exposed to the same stimulus, any differences in gene expression detected are a function of differential gene expression between the strains tested. Stimuli relevant to induction of virulence gene expression in *H. pylori* include adherence to gastric epithelial cells, exposure to acid pH, exposure to agents such as omeprazole, or experimental conditions that simulate gastric motility or osmolarity.

Mutant *H. pylori*

A mutant *Helicobacter pylori* in which the product of the iceA gene is nonfunctional is provided. The mutant can either not express IceA or express a non-functioning IceA antigen. In one example, the mutant *H. pylori* strain is obtained by making an insertional mutation in the coding sequence for the IceA antigen. Briefly, *Campylobacter coli* kanamycin resistance gene (49) is inserted into a unique restriction site of a plasmid that contains the iceA open reading frame. To inactivate the iceA gene of *H. pylori*, the km construct, which is unable to replicate in *H. pylori*, is introduced directly into *H. pylori* by electroporation, as described previously (47). Transformants are selected on blood agar plates containing kanamycin (40 µg/ml) and the mutants are characterized by Southern hybridizations for kanamycin insertion in the iceA gene.

Because other strains expressing IceA can now be identified based on the disclosure of the iceA gene, the iceA genes of other *H. pylori* strains can be mutagenized to produce a mutant of the invention. Since the present invention provides the nucleic acid encoding IceA, other methods of mutating the coding sequence of the IceA can be used to obtain other mutant strains as contemplated herein.

Additional isogenic mutants can be prepared, for example, by inserting a nucleic acid in the iceA gene or deleting a portion of the IceA gene so as to render the gene non-functional or produced in such low amounts that the organism is non-ulcerative. Furthermore, by providing the nucleotide sequence for the nucleic acid encoding IceA, the present invention permits the making of specific point mutations having the desired effect. The deletion, insertion or substitution mutations can be made in the gene sequence in either the regulatory or coding region to prevent transcription or to render the transcribed product nonfunctional.

Non-isogenic mutants are also within the scope of the invention. For example, a live attenuated *H. pylori* that is an iceA⁻recA⁻ or an iceA⁻vacA⁻ mutant according to the present invention, is provided. An IceA⁻recA⁻ mutant strain, an iceA⁻vacA⁻ strain or an IceA⁻vacA⁻recA⁻ mutant strain is constructed, for example, by insertion mutation of the iceA and vacA and recA genes, according to the methods taught herein for iceA, as taught in U.S. Pat. No. 5,434,253 for recA, and as taught in U.S. application Ser. No. 08/200, 232 for vacA. Any of the well known methods of mutating a gene can be used in the present invention to generate *H. pylori* mutant strains. The strains can be tested as provided for immunogenicity.

One approach to the construction of a deletion or insertion mutant is via the Donnenberg method (33). A deletion in iceA is created by deleting a fragment of iceA and religating the iceA clone. This mutant is cloned into suicide vector pILL570. The sacB gene of *Bacillus subtilis* can also be cloned into the suicide vector to provide a conditionally lethal phenotype. This construct can be transformed into *H. pylori* by electroporation, and transformants selected by spectinomycin resistance. The merodiploid strain which contains the suicide vector and the mutated version of the iceA gene are exposed to sucrose to directly select for organisms that have undergone a second recombination, resulting in the loss of the vector. These and other well known methods of making mutations can be applied to the nucleic acids provided herein to obtain other desired mutations.

Vaccines

The IceA protein, antigenic fragments thereof or mutant *H. pylori* of this invention can be used in the construction of a vaccine. Thus, the invention provides an immunogenic amount of the IceA, immunogenic IceA fragment or mutant *H. pylori* in a pharmaceutically acceptable carrier. The vaccine can be the purified protein, the protein on an intact *H. pylori*, or the protein expressed in *E. coli* or other host. The vaccine can then be used in a method of preventing peptic ulceration or other complications of *H. pylori* infection (including atrophic gastritis and malignant neoplasms of the stomach). A method of immunizing a subject against infection by *H. pylori* comprises administering to the subject an immunogenic amount of mutant *H. pylori* in a carrier for the mutant.

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

The pharmaceutically acceptable carrier in the vaccine of the instant invention can comprise saline or other suitable carriers (48). An adjuvant can also be a part of the carrier of the vaccine, in which case it can be selected by standard criteria based on the antigen used, the mode of administration and the subject (48). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention provides methods of preventing or treating *H. pylori* infection and the associated diseases by administering the vaccine to a subject.

Recently described mouse models can be used to test vaccine strains for immunogenicity and protective response (Marchetti et al. (41) and Tompkins and Falkow (42)). Also, a well-established model is that of gnotobiotic piglets, in which the mutant strain is first fed to the piglets. After a suitable interval, the clearance of the vaccine strain is evaluated. Next, this piglet is challenged with the wild-type strain and the presence or absence of infection is ascertained (Eaton et al. (43) and Eaton et al. (44)). Thus, having provided a mutant strain, the testing of it to determine immunogenicity and protective ability is routine.

Purified Antibodies

A purified monoclonal antibody that specifically binds the IceA or antigenic fragment is provided. A purified monoclonal antibody that specifically binds the IceA 1 variant or antigenic fragment is also provided. A purified monoclonal antibody that specifically binds the IceA 2 variant or antigenic fragment is also provided. The antibody can specifically bind a unique epitope of the antigen or it can also bind epitopes of other organisms. The term "bind" means the well understood antigen/antibody binding as well as other non-random association with an antigen. "Specifically bind" as used herein describes an antibody or other ligand that does not cross react substantially with any antigen other than the one specified, in this case, the IceA antigen or its IceA 1 or IceA 2 variants. Antibodies can be made as described in Harlow and Lane (46). Briefly, purified IceA or an immunogenic fragment thereof can be injected into an animal in an amount and in intervals sufficient to elicit an immune response. Polyclonal antibodies can be purified directly, or spleen cells from the animal can be fused with an immortal cell line and screened for monoclonal antibody secretion. Thus, purified monospecific polyclonal antibodies that specifically bind the antigen are within the scope of the present invention.

A ligand that specifically binds the antigen is also contemplated. The ligand can be a fragment of an antibody or a smaller molecule designed to bind an epitope of the antigen. The antibody or ligand can be bound to a substrate or labeled with a detectable moiety or both bound and labeled. The detectable moieties contemplated within the compositions of the present invention include those listed above in the description of the diagnostic methods, including fluorescent, enzymatic and radioactive markers.

Treatment Methods

Methods of treating peptic ulcers in a subject using the compositions of the present invention are provided. For example, in one such method an amount of ligand (e.g., antibody or antibody fragment) specifically reactive with the IceA of *H. pylori* sufficient to bind the antigen in the subject and improve the subject's clinical condition is administered to the subject. Such improvement results from the ligand interfering with IceA's normal function in inducing inflammation and cellular damage. The ligand can be a purified monoclonal antibody specifically reactive with the antigen, a purified polyclonal antibody derived from a nonhuman animal, or other reagent having specific reactivity with the antigen. Additionally, cytotoxic moieties can be conjugated to the ligand/antibody by standard methods. Examples of cytotoxic moieties include ricin A chain, diphtheria toxin and radioactive isotopes.

Another method of treating peptic ulcers in a subject comprises administering to the subject an amount of a ligand/antagonist for a receptor for the IceA antigen of *H. pylori* sufficient to react with the receptor and prevent the binding of the IceA antigens to the receptor. An antagonist for the receptor is thus contemplated. The result is an improvement in the subject's clinical condition. Alternatively, the treatment method can include administering to the subject an amount of an analogue of a receptor for the antigen to result in competitive binding of the antigen, thus inhibiting binding of the antigen to its wild type receptor. The receptor is localized on cells present in the mucosa (e.g., gastroduodenal mucosa), such as epithelial cells, inflammatory cells, or endothelial cells.

Because the expression of IceA is shown to be associated with gastric carcinoma, the above treatment methods are applicable to the treatment or prevention of gastric carcinoma.

The following examples are intended to illustrate, but not limit, the invention. While they are typical of those that might be used, other procedures known to those skilled in the art may be alternatively employed.

EXAMPLES

*H. pylori* strains and cell lines used for adherence.

*H. pylori* strains J166 and J178 were clinical isolates that produced a functional vacuolating cytotoxin and were cagA$^+$. These strains were isolated from persons with peptic ulcer disease and gastritis, respectively. Each strain was grown in Brucella broth with 5% fetal bovine serum (FBS; Gibco, BRL) for 48 hours, harvested by centrifugation (2000×g), and resuspended in RPMI 1640 with 10% FBS. An aliquot was removed for control broth-grown cells and incubated at 37° C, 5% $CO_2$ for one hour (FIG. 1A). The remaining bacteria ($10^9$/well) were co-cultured with AGS cells ($10^6$/well, ATCC CRL 1739, a human gastric adenocarcinoma epithelial cell line) grown in RPMI 1640 with 10% FBS. After 60 minutes, the supernatant containing non-adherent bacteria was removed and centrifuged at 2000×g (nonadherent) and the monolayer of AGS cells and adherent *H. pylori* was trypsinized. Following detachment of the eukaryotic cells and bacteria, trypsin was neutralized by addition of FBS to 10% final volume; 10 volumes of distilled water were then added to the suspension to lyse the AGS cells. Centrifugation (150×g) removed large debris and non-lysed AGS cells. The supernatant was then centrifuged (2000×g) to sediment bacteria that had been adherent to AGS cells (adherent). The control aliquot of broth-grown cells not exposed to AGS cells was harvested simultaneously. The three *H. pylori* pellets (broth, nonadherent, adherent) from each strain (J166, J178) then were frozen at −70° C.

RNA Isolation and RAP RT-PCR.

Total RNA from broth-grown, nonadherent, and adherent *H. pylori* was isolated using the guanidinium thiocyanate-phenol chloroform method (18) and treated with DNase (1 unit/ug). RNA (400 ng) was reverse transcribed to cDNA (19) using random primer 14307 (12) (5'ggttgggtgagaattgcacg). PCR then was performed using 14307 as both the 3' and 5' primers and as template either genomic DNA (20) (positive control), RNA that had not been reverse transcribed (negative control), or cDNA. PCRs included 40 ng template in 50 μl with 3 mM $MgCl_2$, 0.16 μM primer for 4 cycles [94° C., 5 min; 40° C., 5 min; 72° C., 5 min] followed by 30 cycles [94° C., 1 min; 55° C., 1 min; 72° C., 2 min] and a 10 minute extension at 72° C. Amplification products were examined by gel electrophoresis and ethidium bromide staining.

Screening of genomic library and sequencing techniques.

A genomic λZAPII library from *H. pylori* reference strain 60190 (21) was screened with the $^{32}$P-labelled 900 bp PCR product identified by RAP RT-PCR in *H. pylori* clinical isolate J166 (20). Positive plaques were purified, cloned into pBluescript (Stratagene, La Jolla, Calif.), and plasmids containing the cloned DNA inserts were excised by coinfection with helper phage as detailed previously (22). Plasmids were isolated and nucleotide sequence determined unambiguously on both strands using multiple primers and both automated (23) and manual (24) techniques. For PCR product sequencing, bands were excised from agarose gels, subcloned into pT7Blue (Novagen, Madison, Wis.) and sequenced using multiple primers and automated techniques.

Nucleotide sequences were compiled and analyzed using a BLAST search of the GenBank-EMBL databases and GCG Pileup program (23). Predicted amino acid sequences were compared using BLASTP search of the non-redundant protein database (comprised of SWISS-PROT, PIR, Genpept and Brookhaven protein data bank) maintained by the National Center for Biotechnology Information on Jan. 18, 1996.

Clinical specimens.

H. pylori isolates were obtained from patients at the Nashville DVA Medical Center Gastroenterology Clinic during upper endoscopy as described (25). Patients with peptic ulcer disease who were ingesting NSAID medications were excluded. To isolate H. pylori strains, gastric biopsies were placed immediately in normal saline at 4° C. and coarsely homogenized in 250 µl normal saline using a tissue grinder (Micro Kontes, Vineland N.J.). 50 µl was plated onto Trypticase soy agar with 5% sheep blood (BBL) and incubated for 96 hours under microaerobic conditions, as described previously (25).

PCR and cytotoxin assay.

Genomic DNA was extracted (20) from H. pylori isolates and used as template for PCR. iceA-spanning PCR primers ser-1 and meth-3 were designed based on genomic sequence of the H. pylori cysE homolog and M. Hpyl, respectively (FIG. 2) and used to amplify genomic DNA from 6 clinical H. pylori strains. PCRs included 50 ng genomic DNA, 0.5 µM primers, 1.0 µM $MgCl_2$, in 50 µl buffer as described (19). Reactions were amplified for 35 cycles |94° C., 1'; 65° C., 1'; 72° C., 2'| and 1 cycle 72° C., 7'. iceA 2 primers (178-1, 178-2, FIG. 2) were designed based on iceA sequence from H. pylori strain J178. Reactions were amplified for 30 cycles |94° C., 1'; 54° C., 1'; 72° C., 1'| and 1 cycle 72° C., 7'.

PCRs for cagA, vacA m1 mid-region allele, and vacA s1 signal sequence allele were performed using genomic DNA as template, as previously described (19,26). Functional cytotoxin activity was determined by an in vitro HeLa cell assay (26).

RNA/DNA slot blot and Northern hybridization.

DNA (2 ug) and RNA (5 ug) were prepared from strains J166 and J178 grown in broth alone or following co-culture with AGS cells (FIG. 1A). Nucleic acids were denatured, applied to a nylon membrane by slot blotter and hybridized sequentially with the following $^{32}P$-labelled PCR-generated cDNA probes: iceA 1 from strain 60190 (nucleotide positions 264 to 801, [FIG. 2]), iceA 2 from strain J178 (nucleotide positions 1 to 941, [FIG. 2]), cysE from 60190 (nucleotide positions 53 to 434, accession #U43917), M. Hpyl from 60190 (nucleotide positions 1311 to 1987, accession #U43917), and 16S rRNA from 60190 |522 bp product amplified using H. pylori 16S rRNA primers HP1, 5'gctaagagatcagcctatgtcc, and HP2, 5'tggcaatcagcgtcaggtaatg, as described (27)|. Hybridizations were performed and blots were exposed for 24 hours before development, as described (20).

For Northern hybridizations, RNA samples were prepared as described above, electrophoresed in denaturing agarose gels and transferred to nylon. Nylon blots were hybridized, washed and exposed for 24–48 hours before development, as described (20).

Statistics. The 2-tailed Fisher's exact test was used for statistical analyses.

RAP RT-PCR identified a strain-specific cDNA product induced by adherence to AGS cells.

Figure 1B:
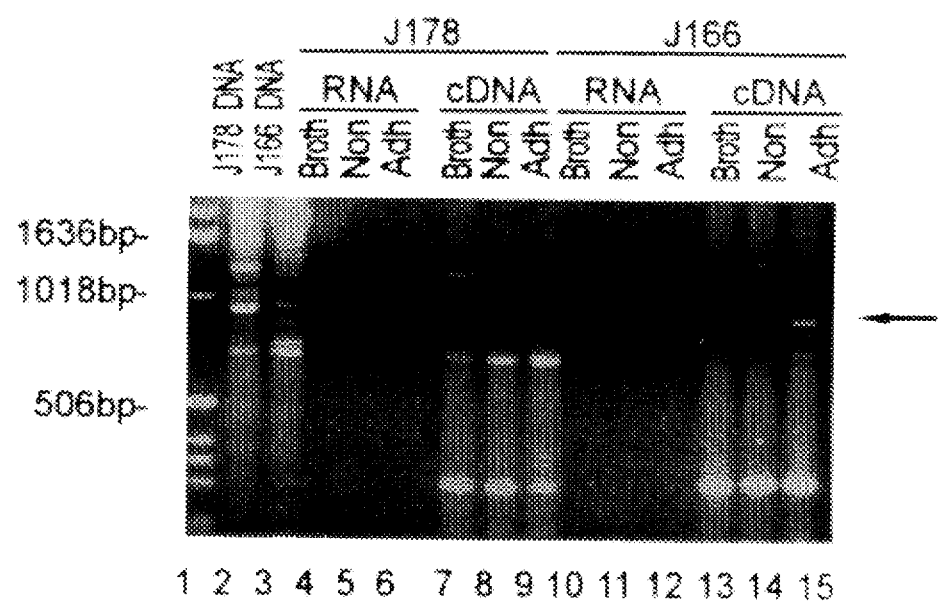
FIG. 1B shows RAP PCR and RAP RT-PCR of DNA and RNA from strains J178 and J166. PCR was performed using the same random primer and either genomic DNA, RNA that had not been reverse transcribed, or cDNA as template. Broth, broth-grown bacteria not exposed to AGS cells; Non, non-adherent bacteria in AGS cell supernatant; Adh, bacteria adherent to AGS cells. Lane 1, molecular size markers; Lanes 2–3, DNA from strains J178 and J166, respectively; Lanes 4–6 and 10–12, RNA from strains J178 and J166, respectively, that had not been reverse transcribed; Lanes 7–9 and 13–15, RNA from strains J178 and J166, respectively, that had been reverse transcribed prior to PCR.

To determine whether adherence to gastric epithelial cells induced strain-selective expression of novel H. pylori genes, we performed random arbitrarily-primed reverse transcriptase-PCR (RAP RT-PCR) on RNA isolated from two cagA$^+$, tox$^+$ H. pylori strains (J166 and J178 isolated from patients with ulcer disease or gastritis alone, respectively) after co-culture with AGS gastric epithelial cells or after growth in broth only. As a positive control, genomic DNA from each isolate was used as template for RAP PCR. PCR using genomic DNA demonstrated highly different amplification patterns, as expected (12) (FIG. 1B); however, RAP RT-PCR yielded a much more limited array of conserved and non-conserved products in the two strains (FIG. 1B). For strain J166, a product of approximately 900 bp was amplified from bacteria that adhered to AGS cells, but not from broth-culture or non-adherent bacteria (FIG. 1B). This product was not amplified from strain J178 under any growth condition. No PCR amplification was observed with RNA that had not been reverse transcribed, indicating the lack of contamination by genomic DNA that could serve directly as a PCR template.

To address whether the gene encoding the transcript induced by adherence differed between strains, the 900 bp PCR product from J166 was subcloned and DNA sequence was determined. The sequence identified an open reading frame not previously reported, which we designated iceA ( induced by contact with epithelium). Primers specific for iceA were used to PCR-amplify genomic DNA from 40 H. pylori clinical isolates, and the cagA$^+$tox$^+$ reference strain 60190. Amplification patterns differed among strains, indicating genomic variation in icea (not shown). These data indicated that adherence to gastric epithelial cells induced the expression of a novel H. pylori gene, iceA, which may possess sequence diversity. The iceA sequence from strain 60190 is deposited as follows: GenBank accession numbers; icea, cysE, M.Hpyl #U43917.

iceA is flanked by highly conserved genes.

To obtain genomic sequence of iceA and flanking genes, we screened a genomic λZAPII library from reference strain 60190 (21) with the 900 bp RAP RT-PCR J166 product. Strain 60190 was chosen as the source of the genomic clone because genomic DNA from this strain and the prototype ulcer strain J166 gave identical PCR patterns with iceA primers. In the genomic clone isolated, pRMP100, (FIG. 2), three open reading frames were identified. Upstream of the iceA ORF, we identified the 3' terminus of a gene not previously described in H. pylori with strong homology to a serine acetyltransferase (cysE) of Bacillus stearothermophilus (GenBank accession #E53402) (28)]. The 3' terminus of cysE extends from nucleotide 1 to 121 for each strain. An ORF immediately downstream of iceA had strong homology to a DNA adenine methyltransferase in Neisseria lactamica (M.N1aIII) (accession #P24582) (29)| and was designated M.Hpyl. The 5' terminus of M. Hpyl extends from nucleotide 900 to 975 and 866 to 941 for strains 60190 and J178, respectively. A potential 384 bp iceA ORF from 60190 was initiated by a canonical ATG codon at position 508 (FIG. 2) and a potential ribosome binding site (AGCA) ended 13 bp upstream. iceA encoded a predicted protein of 127 amino acid residues with a calculated molecular weight of 14.7 kDa, with no significant homology to any previously reported bacterial proteins. An alternative translation initiation codon in the same frame is TTG at nucleotide 355 and its subsequent amino acid sequence is shaded in FIG. 2. The potential iceA ORFs from 60190 genomic DNA and the iceA sequence of the J166 RAP RT-PCR product showed 86.1% nucleotide identity, confirming the sequence relatedness first suggested by PCR. A potential ORF within J178 iceA commences at nucleotide 357 and ends at nucleotide 536.

Multiple alternative TTG initiation codons were present upstream of the putative ATG translation start site at position 508 codon within the same open reading frame. Although the use of TTG as an initiation codon has been described in other bacteria (30), it has not been observed previously in H. pylori. In addition, several GTG codons which could encode initiating methionine residues were present downstream of the ATG at position 508. It is currently unknown which of these codons represents the translational start site. It is also possible that both translational start codons are used, there are examples of proteins that have two or more translation initiation sites, and the resultant proteins differ in their function. This apparently is more common in viruses and eukaryotic cells than in prokaryotes. An example in eukaryotes is the protein basic fibroblast growth factor (bFGF). It has four alternate translation initiation sites; 3 of these result in inclusion of an N-terminal extension that encodes a nuclear localization signal which targets the protein to the nucleus, while the other isoform lacks this N-terminal sequence and remains localized to the cytoplasm.

To investigate potential iceA sequence diversity among *H. pylori* isolates, PCR primers which spanned iceA were designed. iceA was amplified from genomic DNA of the gastritis strain J178, and sequence analysis showed a homologous ORF (FIG. 2). However, the iceA sequences in 60190 and J178 shared only 39.9% nucleotide identity, confirming that substantial allelic variation of iceA exists. The longest possible ORF in J178 DNA predicts a protein of 57 amino acids. The iceA alleles present in strains 60190 and J178 were designated 1 and 2, respectively, and their diversity contrasted markedly with the nearly complete sequence conservation of the flanking genes, cysE and *M. Hpyl* (FIG. 2).

iceA allelic variation is associated with peptic ulcer disease.

Figure 3A:
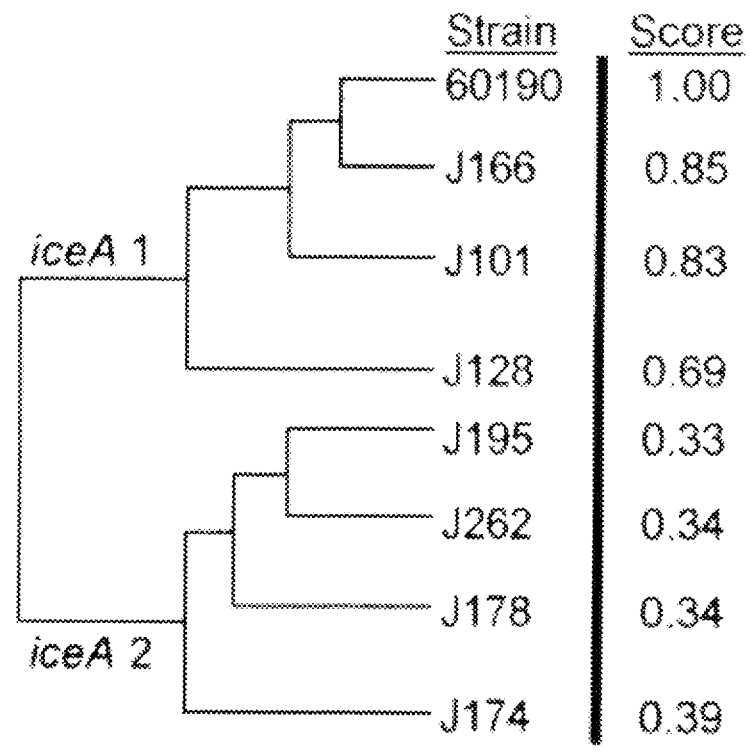
FIG. 3A shows a dendogram demonstrating relatedness of iceA alleles among 8 *H. pylori* strains and showing that iceA allelic variation exists among *H. pylori* clinical isolates. PCR products were sequenced and progressive, pairwise alignments of iceA-homologous DNA regions were performed. Scores that reflect the similarities of iceA sequences relative to that of strain 60190 are shown at right (37). Strains J166, J101, and J128 were isolated from patients with duodenal ulcer disease; strains J195, J262, J178, and J174 were isolated from patients with gastritis only. The clinical status of the source patient for reference strain 60190 is unknown.
Figure 3B:
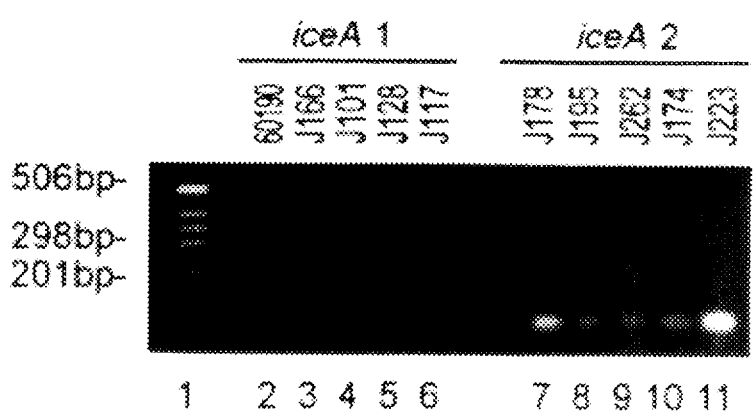
FIG. 3B shows a representative PCR on genomic DNA from clinical *H. pylori* isolates using iceA 2 primers 178-1 and 178-2 derived from J178 iceA sequence (FIG. 2) showing that iceA allelic variation exists among *H. pylori* clinical isolates. iceA 1 strains (lanes 2–6) demonstrated no amplification products, iceA 2 strains (lanes 7–11) consisted of a single product of the predicted size. Lane 1, molecular size markers.

To characterize iceA genotypes more definitively, sequences of PCR products generated with iceA-spanning primers from 5 additional clinical isolates (25) were compared with iceA sequence from the prototype ulcer (J166) and gastritis (J178) strains and reference strain 60190. Progressive pairwise alignments of iceA-homologous DNA regions demonstrated 2 major allelic families (FIG. 3A), iceA 1 (60190-like) and iceA 2 (J178-like) which correlated with the clinical outcome of infection (ulcer vs. gastritis only). To confirm the suggested relationship between iceA genotypes and peptic ulceration, PCR was performed using genomic DNA from 40 *H. pylori* clinical isolates (25), with primers designed to amplify the iceA 2 allele from strain J178 (FIG. 2). Amplification patterns with J178 iceA 2 primers differed between strains (FIG. 3B). Thirty strains showed a single product of the same size as that for J178 and were classified as iceA 2 strains. Eight (27%) of these strains were from patients with ulcer disease. In contrast, ten isolates, including 3 with iceA 1 sequence (FIG. 3A), gave no amplification products and were classified as iceA 1 strains; all ten strains had been isolated from patients with ulcer disease (p<0.001 versus iceA 2) (Table 1). These results demonstrate that iceA exists in at least two major allelic forms and that strains possessing the iceA 1 allele are strongly associated with peptic ulcer disease.

TABLE 1

Correlation of iceA allelic variation* with duodenal ulcer disease, cagA genotype, vacA mid-region and signal sequence types and functional cytotoxin activity.

| iceA allele | DU (%)† | cagA⁺ (%)‡ | vacA m1 mid-region allele (%)§ | vacA s1 signal allele (%)§ | Toxigenicity (%)¶ |
|---|---|---|---|---|---|
| iceA 1 (n = 10) | 100 | 70 | 30 | 80 | 56 |
| iceA 2 (n = 30) | 27 | 53 | 40 | 60 | 48 |
| p-value** | 0.0005 | 0.47 | 0.71 | 0.45 | 1.0 |

*iceA alleles identified by PCR as shown in Figure 3B.

TABLE 1-continued

Correlation of iceA allelic variation* with duodenal ulcer disease, cagA genotype, vacA mid-region and signal sequence types and functional cytotoxin activity.

| iceA allele | DU (%)† | cagA⁺ (%)‡ | vacA m1 mid-region allele (%)§ | vacA s1 signal allele (%)§ | Toxigenicity (%)¶ |
|---|---|---|---|---|---|

†Duodenal ulcer (DU) disease defined as a circumscribed break in the mucosa with diameter of at least 1cm, with apparent depth and covered by an exudate noted on either current or prior endoscopy. Patients with duodenal ulcer disease who were ingesting NSAID medications were excluded.
‡Presence of cagA determined by PCR of *H. pylori* genomic DNA and by RT-PCR of gastric tissue, as described (19).
§vacA signal sequence and mid-region alleles determined by PCR amplification of genomic DNA, as previously described (26).
¶Functional cytotoxin activity determined by in vitro HeLa cell assay, (26).
**p-value by 2-tailed Fishers exact test.

Adherence to gastric epithelium induced the monocistronic expression of iceA 1.

The existence of iceA allelic variants demonstrated above suggests the possibility that expression of the iceA 2 allele in J178 following adhesion might not have been detected using the random primer in our original RAP RT-PCR experiment.

Figure 4:
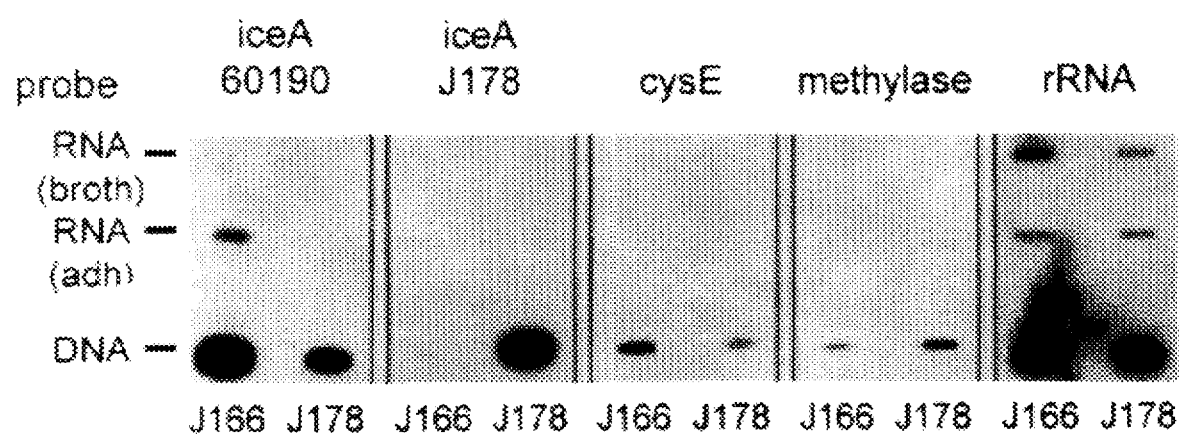
FIG. 4 shows that iceA 1 RNA is expressed following adherence.

Therefore, we examined RNA from both prototype strains (J166 and J178) using allele-specific cDNA probes for hybridization in slot blot (FIG. 4) and Northern analyses. DNA (2 ug) and RNA (5 ug) was prepared from strains J166 and J178 grown in broth alone or following co-culture with AGS cells (adh) (as described in FIG. 1), denatured, and applied to a nylon membrane. The membrane was hybridized sequentially with the following ³²P-labelled PCR-generated cDNA probes: iceA 1 from strain 60190, iceA 2 from strain J178, cysE from 60190, *M.Hpyl* from 60190, and 16S rRNA from 60190.

iceA expression was markedly up-regulated in ulcer-strain J166 only following adherence; iceA expression was not detected in gastritis-strain J178 under any condition. Using an iceA 1 cDNA probe generated from strain 60190 on slot blots, iceA expression in J166 was found to be significantly up-regulated by adherence to AGS cells in comparison to broth-growth alone, but there was no hybridization to RNA from strain J178 following broth-growth or adherence. As a positive control, genomic DNA from each strain was probed on the same blot and demonstrated strong hybridization signals. When the blot was stripped and rehybridized using a probe for the J178 iceA 2 allele, there was no detectable iceA expression in RNA from either broth-grown or adherent cells of either strain. Northern analysis using an iceA 1 probe confirmed the substantial up-regulation of J166 iceA following adherence and a transcript size of 350–550 bp. When probes for the conserved flanking genes cysE and *M.Hpyl* were used, no expression was found in either *H. pylori* strain under either growth condition, in both slot-blot (FIG. 4) and Northern analyses. These results indicate that iceA expression is strain-selective, monocistronic, and induced by adherence of *H. pylori* to gastric epithelial cells in vitro.

iceA alleles are not correlated with known *H. pylori* virulence determinants.

Since iceA 1 was associated with peptic ulcer disease, we examined the relationship between icea alleles and other markers of *H. pylori* virulence (Table 1). There were no significant correlations between iceA alleles and cagA genotype, vacA mid-region or signal sequence alleles, or in vitro cytotoxin activity (toxigenicity), indicating independence of iceA 1 from previously described *H. pylori* virulence markers.

Conclusion.

The following features of iceA predict that it is a virulence gene. First, iceA was significantly up-regulated by adherence to gastric epithelial cells. *H. pylori* binding to gastric mucosal cells is an obligate, early event in the establishment of chronic infection (16,17). Transition of *H. pylori* from spiral to coccoid forms occurs following adherence, suggesting that the bacteria receive stimuli from eukaryotic cells that may modulate gene expression (15). Attachment of *H. pylori* to AGS cells is characterized by effacement of the eukaryotic cell microvilli, pedestal formation, cytoskeletal rearrangement, and phosphorylation of host cell proteins (15). Adherence of enteropathogenic *E. coli* (EPEC) induces similar morphologic features, and modification of eukaryotic cell signal transduction pathways has been identified in EPEC, *S. typhimurium*, and *Yersinia pseudotuberculosis* (31–34). A property common to each of these mucosal pathogens is that interaction with mammalian cells induces bacterial gene expression critical to pathogenesis. Thus, for *H. pylori*, contact with gastric epithelial cells in vivo and in vitro is one paradigm for induction of virulence genes.

Second, iceA exists in two major allelic variants, but only the iceA 1 allele was up-regulated following adherence with gastric epithelium. This finding was consistent, regardless of the techniques (RAP RT-PCR, RNA slot blots, Northern analysis) or the probes (iceA 1, iceA 2) used to detect iceA expression. The iceA 1 allele was present in a minority of strains examined (25% in our population) which is provocative, considering that only a small percentage (10–20%) of *H. pylori*-infected persons develop clinical or pathologic sequelae (peptic ulcer disease or gastric cancer) (5). Toxigenicity and cagA genotype are strain-specific traits found more commonly in ulcer-derived *H. pylori* strains, however, these traits also are present in the majority of *H. pylori* strains derived from persons who remain asymptomatic. These data contrast with the presence of iceA 1 in a minority of strains. Further, iceA alleles were not correlated with presence of cagA, vacA signal sequence or mid-region alleles, or in vitro cytotoxin activity. These findings suggest evolutionary divergence in a subset of strains with increased virulence.

Third, iceA 1 genotype was highly associated with peptic ulcer disease. All strains possessing the iceA 1 allele were isolated from patients with ulceration in contrast to only 27% of strains with the iceA 2 allele, suggesting that infection with iceA 1 strains may significantly increase the risk for subsequent ulcer development. Treatment of *H. pylori* is complex, involving regimens with multiple dosing schedules and toxicities, and patient compliance often is suboptimal. The identification of *H. pylori*-infected persons who are at increased risk for developing clinical complications should enable physicians to focus therapeutic efforts. Further, delineating the means by which particular *H. pylori* clinical isolates lead to injury will contribute to the overall understanding of chronic mucosal infectious processes.

In summary, the experiments reported here demonstrate that adherence of *H. pylori* to gastric epithelial cells induces strain-specific expression of a novel ulcer-associated gene, iceA, which exists in two major allelic variants. The increased expression of iceA following adherence and its association with peptic ulcer disease suggest it may play a role in determining increased virulence. iceA allelic variation is expected to be useful for determining the risk of developing ulcer disease.

Construction of IceA mutant *H. pylori*.

To study the role of the IceA protein of *H. pylori* in virulence, toxin secretion, and antigenicity, the IceA gene was inactivated. A *Campylobacter coli* kanamycin resistance gene (Labigne-Roussel et al. Gene transfer from *Escherichia coli* to Campylobacter species. Development of shuttle vectors for genetic analysis of *Campylobacter jejuni*. J. Bacteriol. 169:5320–5323, 1987) is inserted into a unique restriction site of a plasmid that contains the iceA open reading frame. To inactivate the iceA gene of *H. pylori*, the km constructs, that is unable to replicate in *H. pylori*, is introduced directly into *H. pylori* by electroporation, as described previously (47). Transformants are selected on blood agar plates containing kanamycin (40 µg/ml) and the mutants are characterized by Southern hybridizations for kanamycin insertion in the iceA gene.

IceA Expression.

Several attempts have been made to subclone the cDNA for iceA 1 into several vectors for expression as a fusion protein in order to prepare purified protein for ELISAs, making antibodies, etc. In the most recent experiment, a commercial vector (pGEX2) was used, which includes the gene encoding glutahione-S-transferase upstream of sequence encoding amino acids that result in a thrombin cleavage site, followed by a restriction enzyme cloning cassette. The cDNA for the 21 kDa form of iceA 1 was cloned into this vector, the 50 kDa fusion protein was purified on glutahione argarose, dialyzed the glutathione out, then cleaved the fusion protein with thrombin. This resulted in two bands on SDS-PAGE, one of 29 kDa corresponding to GST and a second band of about 21 kDa which appears to be IceA 1. The potentially interesting which appears to be IceA 1. The potentially interesting finding is that the first several times this was attempted, only a very faint low molecular weight band was obtained when the fusion protein was cleaved with thrombin and no band at 21 kDa. In the successful experiment several protease inhibitors were included at all stages of the purification. There may proteases derived from the *E. coli* that are cleaving IceA or IceA itself could be a protease that is autocatalytic. The latter would be quite interesting since it is relevant to the protein's function.

Throughout this application various publications are referenced by numbers within parentheses. Full citations for these publications are as follows. The disclosures of these publications in their entireties are hereby incorporated by reference into this application in order to more fully describe the state of the art to which this invention pertains.

REFERENCES

1. Dooley, C. P., Fitzgibbons, P. L., Cohen, H., Appleman, M. D., Pérez-Pérez, G. I. & Blaser, M. J. (1989) *N. Engl. J. Med.* 321, 1562–1566.
2. Peterson, W. L. (1991) *N. Engl. J Med* 324, 1043–1048.
3. Nomura, A., Stemmermann, G. N., Chyou, P., Kato, I., Pérez-Pérez, G. I. & Blaser, M. J. (1991) *N. Engl. J. Med.* 325, 1132–1136.
4. Parsonnet, J., Hansen, S., Rodriguez, L., Gelb, A. B., Warnke, R. A., Jellum, E., Orentreich, N., Vogelman, J. H. & Friedman, G. D. (1994) *N. Engl. J. Med.* 330, 1267–1271.
5. Hopkins, R. J. & Morris, J. G. (1994) *Am. J. Med.* 97, 265–277.
6. Leunk, R. D., Johnson, P. T., David, B. C., Kraft, W. G. & Morgan, D. R. (1988) *J. Med. Microbiol.* 26, 93–99.
7. Ghiari, P., Marchetti, M., Blaser, M. J., Tummuru, M. K. R., Cover, T. L., Segal, E. D., Tompkins, L. S. & Rappuoli, R. (1995) *Infect. Immun.* 63, 4154–4160.
8. Cover, T. L., Dooley, C. P. & Blaser, M. J. (1990) *Infect. Immun.* 58, 603–610.

9. Crabtree, J. E., Figura, N., Taylor, J. D., Bugnoli, M., Armellini, D. & Tompkins, D. S. (1992) *J Clin Pathol.* 45, 733–734.
10. Crabtree, J. E., Taylor, J. D., Wyatt, J. I., Heatley, R. V., Shallcross, T. M., Tompkins, D. S. & Rathbone, B. J. (1991) *Lancet* 338, 332–335.
11. Figura, N., Guglielmetti, P., Rossolini, A., Barberi, A., Cusi, G., Musmanno, R. A., Russi, M. & Quaranta, S. (1989) *J Clin Microbiol.* 27, 225–226.
12. Akopyanz, N., Bukanov, N. O., Westblom, T. U., Kresovich, S. & Berg, D. E. (1992) *Nucleic. Acids. Res.* 20, 5137–5142.
13. Mekalanos, J. J. (1992) *J. Bacteriol.* 174, 1–7.
14. Rosqvist, R., Magnusson, K. E. & Wolf-Watz, H. (1994) *EMBO J.* 13, 964–972.
15. Segal, E. D., Falkow, S. & Tompkins, L. S. (1996) *Proc. Natl. Acad. Sci. U. S. A.* 93, 1259–1264.
16. Hessey, S. J., Spencer, J., Wyatt, J. I., Sobala, G., Rathbone, B. J., Axon, A. T. & Dixon, M. F. (1990) *Gut* 31, 134–138.
17. Kirschner, D. E. & Blaser, M. J. (1995) *J. Theor. Biol.* 176, 281–290.
18. Chomczynski, P. & Sacchi, N. (1987) *Ann. Biochem.* 162, 156–159.
19. Peek, R. M., Miller, G. G., Tham, K. T., Pérez-Pérez, G. I., Cover, T. L., Atherton, J. C., Dunn, D. G. & Blaser, M. J. (1995) *J. Clin. Microbiol.* 33, 28–32.
20. Maniatis, T., Fritsch, E. F. & Sambrook, J. (1982) *Molecular cloning: A laboratory manual*, Cold Spring Harbor Laboratory: Cold Spring Harbor, Mass.
21. Cover, T. L., Tummuru, M. K. R., Cao, P., Thompson, S. A. & Blaser, M. J. (1994) *J. Biol. Chem.* 269, 10566–10573.
22. Short, J. M., Fernandez, J. M., Sorge, J. A. & Huse, W. D. (1988) *Nucleic Acids Res.* 16, 7583–7600.
23. Thompson, S. A. & Blaser, M. J. (1995) *Infect. Immun.* 63, 2185–2193.
24. Sanger, F., Nicklen, S. & Coulson, A. R. (1977) *Proc. Natl. Acad. Sci. U. S. A.* 74, 5463–5467.
25. Peek, R. M., Miller, G. G., Tham, K. T., Pérez-Pérez, G. I., Zhao, X. M., Atherton, J. C. & Blaser, M. J. (1995) *Lab. Invest.* 71, 760–770.
26. Atherton, J. C., Cao, P., Peek, R. M. Jr., Tummuru, M. K. R., Blaser, M. J. & Cover, T. L. (1995) *J. Biol. Chem.* 270, 17771–17777.
27. Engstrand, L., Nguyen, A. M., Graham, D. Y. & el Zaatari, F. A. (1992) *J. Clin. Microbiol.* 30, 2295–2301.
28. Gagnon, Y., Breton, R., Putzer, H., Pelchat, M., Grunberg-Manago, M. & Lapointe, J. (1994) *J. Biol. Chem.* 269, 7473–7482.
29. Labbe, D., Holtke, H. J. & Lau, P. C. K. (1990) *Mol. Genetics* 224, 101–110.
30. Hershey, J. W. B. (1987) *Escherichia coli and Salmonella typhimurium: Cellular and Molecular Biology*, American Society for Microbiology: Washington, D.C. pp. 621–622.
31. Moon, H. W., Whipp, S. C., Argenzio, R. A., Levine, M. M. & Giannella, R. A. (1988) *Infect. Immun.* 41, 1340–1351.
32. Rosenshine, I., Donnenberg, M. S., Kaper, J. B. & Finlay, B. B. (1992) *EMBO J.* 11, 3551–3560.
33. Galan, J. E., Pace, J. & Hayman, M. J. (1992) *Nature* 357, 588–589.
34. Rosenshine, I., Duronio, V. & Finlay, B. B. (1992) *Infect. Immun.* 60, 2211–2217.
35. Liang, P. & Pardee, A. B. (1992) *Science* 257, 967–971.
36. Wong, K. K. & McClelland, M. (1994) *Proc. Natl. Acad. Sci. U. S. A.* 91, 639–643.
37. Devereux, J., Haeberli, P. & Smithies, O. (1984) *Nucleic Acids Res.* 12, 387–395.
38. Cunningham, et al. (1989) *Science*, 243:1330–1336.
39. Ferretti, et al., (1986) *Proc. Nat. Acad. Sci.* 82:599–603.
40. Tummuru, M. K. R., T. Cover, and M. J. Blaser. (1993). *Infect. Immun.* 61:1799–1810.
41. Marchetti, M., Arico, B., Burroni, D., Figura, N., Rappuoli, and R., Ghiara P. (1995) *Science.* 107:1573–1578.
42. Tompkins, Lucy S. and Stanley Falkow (1995) *Science* 267:1821–1822).
43. Eaton, J. A., C. L. Brooks, D. R. Morgan, and S. Krawowka (1991) *Infect. Immun.* 59:2470–5; 26.
44. Eaton, J. A., D. R. Morgan and S. Krakowka (1992) *J. Med. Microbiol.* 37:123–7.
45. Pei, Z., Ellison, R. T., Blaser, M. J. (1991) *J. Biol. Chem.* 266:16363–16369.
46. Harlow and Lane, *Antibodies: A Laboratory Manual*, Cold Spring Harbor Laboratory, Cold Spring Harbor, N.Y., 1988.
47. Ferrero, R. L., V. Cussac, P. Courcoux, and A. Labigne. (1992) *J. Bacteriol.* 174:4212–4217.
48. Arnon, R. (Ed.) (1987) *Synthetic Vaccines I*:83–92, CRC Press, Inc., Boca Raton, Fla.
49. Labigne-Roussel et al. Gene transfer from *Escherichia coli* to Campylobacter species. Development of shuttle vectors for genetic analysis of *Campylobacter jejuni*. *J. Bacteriol.* 169:5320–5323, 1987.

---

What is claimed is:

1. An isolated nucleic acid molecule that encodes an IceA 1 or 2 (induced by contact with epithelium), protein of *Helicobacter pylori*.

2. An isolated nucleic acid molecule that encodes a *Helicobacter pylori*-specific, IceA 1 or 2-specific immunogenic fragment of an IceA protein of *Helicobacter pylori*.

3. An isolated nucleic acid molecule that encodes the amino acid sequence defined in the Sequence Listing as SEQ ID NO:2.

4. An isolated nucleic acid molecule that encodes the amino acid sequence defined in the Sequence Listing as SEQ ID NO:7.

5. An isolated nucleic acid molecule that encodes the the amino acid sequence defined in the Sequence Listing as SEQ ID NO:101.

6. An isolated nucleic acid molecule that encodes an IceA 1 or 2 protein of *Helicobacter pylori*, wherein the protein comprises one or more amino acid sequence(s) selected from the group consisting of the sequences defined in the Sequence Listing as SEQ ID Nos:64–100.

7. An isolated *Helicobacter pylori*-specific, iceA 1 or 2-specific nucleic acid fragment of a nucleic acid molecule that encodes an IceA 1 or 2 protein of *Helicobacter pylori*.

8. An isolated *Helicobacter pylori*-specific, iceA 1 or 2-specific, at least 25 nucleotide nucleic acid fragment of an iceA 1 or 2 nucleic acid of *Helicobacter pylori*.

9. An isolated iceA 1 or 2 nucleic acid molecule of *Helicobacter pylori*, having the nucleotide sequence defined in the Sequence Listing as SEQ ID NO:1.

10. An isolated iceA 1 or 2 nucleic acid molecule of *Helicobacter pylori*, having the nucleotide sequence defined in the Sequence Listing as SEQ ID NO:6.

11. An isolated iceA 1 or 2 nucleic acid molecule of *Helicobacter pylori*, having the nucleotide sequence defined in the Sequence Listing as SEQ ID NO:3.

12. An isolated iceA 1 or 2 nucleic acid molecule of *Helicobacter pylori*, having the nucleotide sequence defined in the Sequence Listing as SEQ ID NO:4.

13. An isolated iceA 1 or 2 nucleic acid molecule of *Helicobacter pylori*, having the nucleotide sequence defined in the Sequence Listing as SEQ ID NO:5.

14. An isolated iceA 1 or 2 nucleic acid molecule of *Helicobacter pylori*, having the nucleotide sequence defined in the Sequence Listing as SEQ ID NO:8.

15. An isolated iceA 1 or 2 nucleic acid molecule of *Helicobacter pylori*, having the nucleotide sequence defined in the Sequence Listing as SEQ ID NO:9.

16. An isolated iceA 1 or 2 nucleic acid molecule of *Helicobacter pylori*, having the nucleotide sequence defined in the Sequence Listing as SEQ ID NO:10.

17. An isolated iceA 1 or 2 nucleic acid molecule of *Helicobacter pylori*, having the nucleotide sequence defined in the Sequence Listing as SEQ ID NO:63.

* * * * *

SEQUENCE LISTING ( 1 ) GENERAL INFORMATION:

( i i i ) NUMBER OF SEQUENCES: 101

( 2 ) INFORMATION FOR SEQ ID NO:1:

( i ) SEQUENCE CHARACTERISTICS:
        ( A ) LENGTH: 537 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS (B) LOCATION: 1..537

(xi) SEQUENCE DESCRIPTION: SEQ ID NO:1:

| TTG | GCT | AAA | GAA | TTT | AAT | TTG | GAG | TTT | GAT | AAA | GGG | CAA | ACT | CTA | GGA | 48 |
| Leu | Ala | Lys | Glu | Phe | Asn | Leu | Glu | Phe | Asp | Lys | Gly | Gln | Thr | Leu | Gly | |
| 1 | | | | 5 | | | | | 10 | | | | | 15 | | |

| AAT | TCT | ATT | GAT | AGA | ATA | CGC | TTG | AAT | GGC | TAT | AAT | ACC | GAA | TGT | GTT | 96 |
| Asn | Ser | Ile | Asp | Arg | Ile | Arg | Leu | Asn | Gly | Tyr | Asn | Thr | Glu | Cys | Val | |
| | | | 20 | | | | | 25 | | | | | 30 | | | |

| TTT | AAC | CAA | AGT | ATC | TGT | CAA | GAC | ATT | AAA | AAC | CAC | TAT | AAG | CAA | CAA | 144 |
| Phe | Asn | Gln | Ser | Ile | Cys | Gln | Asp | Ile | Lys | Asn | His | Tyr | Lys | Gln | Gln | |
| | | | 35 | | | | | 40 | | | | | 45 | | | |

| TGT | TGC | GCG | ATG | TGT | GGT | GTG | CGT | GGC | AAC | TCT | GAA | AAC | ACT | CAA | ATA | 192 |
| Cys | Cys | Ala | Met | Cys | Gly | Val | Arg | Gly | Asn | Ser | Glu | Asn | Thr | Gln | Ile | |
| | | 50 | | | | | 55 | | | | | 60 | | | | |

| GAA | GTG | GAT | CAT | AAA | GAC | GGC | CGC | AAG | GAT | GAT | TCA | AGA | GTT | TCT | GAT | 240 |
| Glu | Val | Asp | His | Lys | Asp | Gly | Arg | Lys | Asp | Asp | Ser | Arg | Val | Ser | Asp | |
| 65 | | | | | 70 | | | | | 75 | | | | | 80 | |

| TTA | AAC | ACA | CAG | ACT | TTT | GAT | GAT | TTT | CAG | GCT | TTA | TGC | AAA | GCT | TGT | 288 |
| Leu | Asn | Thr | Gln | Thr | Phe | Asp | Asp | Phe | Gln | Ala | Leu | Cys | Lys | Ala | Cys | |
| | | | | 85 | | | | | 90 | | | | | 95 | | |

| AAC | GAT | AAG | AAA | CGC | CAG | ATT | TGT | AAA | AAA | TGC | AAA | GAA | AGT | GGC | TAT | 336 |
| Asn | Asp | Lys | Lys | Arg | Gln | Ile | Cys | Lys | Lys | Cys | Lys | Glu | Ser | Gly | Tyr | |
| | | | 100 | | | | | 105 | | | | | 110 | | | |

| AGA | TTT | GAC | GCA | ACA | AAA | ATT | CCT | GGC | AAT | TAT | TAT | TCT | TTC | TAT | GAG | 384 |
| Arg | Phe | Asp | Ala | Thr | Lys | Ile | Pro | Gly | Asn | Tyr | Tyr | Ser | Phe | Tyr | Glu | |
| | | | 115 | | | | | 120 | | | | | 125 | | | |

| GGG | GAG | GCT | GAA | TAT | GAT | GGT | TGT | GTG | GGC | TGT | TAT | CAA | TAT | GAC | CCC | 432 |
| Gly | Glu | Ala | Glu | Tyr | Asp | Gly | Cys | Val | Gly | Cys | Tyr | Gln | Tyr | Asp | Pro | |
| | 130 | | | | | 135 | | | | | 140 | | | | | |

| ATA | CAA | TAC | AGG | AAA | ACT | TGT | AAT | GAT | AGG | ATA | TAC | AAT | GAA | GGG | TAT | 480 |
| Ile | Gln | Tyr | Arg | Lys | Thr | Cys | Asn | Asp | Arg | Ile | Tyr | Asn | Glu | Gly | Tyr | |
| 145 | | | | | 150 | | | | | 155 | | | | | 160 | |

| CAA | AAA | GGC | TAT | GGT | GAT | GGG | TAT | CAA | ATT | GGA | TAC | CAT | CAA | AAA | ACT | 528 |
| Gln | Lys | Gly | Tyr | Gly | Asp | Gly | Tyr | Gln | Ile | Gly | Tyr | His | Gln | Lys | Thr | |
| | | | | 165 | | | | | 170 | | | | | 175 | | |

| ACT | TTA | TAG | | | | | | | | | | | | | | 537 |
| Thr | Leu | * | | | | | | | | | | | | | | |

(2) INFORMATION FOR SEQ ID NO:2:

(i) SEQUENCE CHARACTERISTICS:
 (A) LENGTH: 178 amino acids
 (B) TYPE: amino acid
 (D) TOPOLOGY: linear (ii) MOLECULE TYPE: protein (xi) SEQUENCE DESCRIPTION: SEQ ID NO:2:

| Leu | Ala | Lys | Glu | Phe | Asn | Leu | Glu | Phe | Asp | Lys | Gly | Gln | Thr | Leu | Gly |
| 1 | | | | 5 | | | | | 10 | | | | | 15 | |

| Asn | Ser | Ile | Asp | Arg | Ile | Arg | Leu | Asn | Gly | Tyr | Asn | Thr | Glu | Cys | Val |
| | | | 20 | | | | | 25 | | | | | 30 | | |

| Phe | Asn | Gln | Ser | Ile | Cys | Gln | Asp | Ile | Lys | Asn | His | Tyr | Lys | Gln | Gln |
| | | | 35 | | | | | 40 | | | | | 45 | | |

| Cys | Cys | Ala | Met | Cys | Gly | Val | Arg | Gly | Asn | Ser | Glu | Asn | Thr | Gln | Ile |
| | | 50 | | | | | 55 | | | | | 60 | | | |

| Glu | Val | Asp | His | Lys | Asp | Gly | Arg | Lys | Asp | Asp | Ser | Arg | Val | Ser | Asp |
| 65 | | | | | 70 | | | | | 75 | | | | | 80 |

| Leu | Asn | Thr | Gln | Thr | Phe | Asp | Asp | Phe | Gln | Ala | Leu | Cys | Lys | Ala | Cys |
| | | | | 85 | | | | | 90 | | | | | 95 | |

|     |     |     |     |     |     |     |     |     |     |     |     |     |     |
| --- | --- | --- | --- | --- | --- | --- | --- | --- | --- | --- | --- | --- | --- |
| Asn | Asp | Lys | Lys | Arg | Gln | Ile | Cys | Lys | Lys | Cys | Lys | Glu | Ser | Gly | Tyr |
|     |     |     | 100 |     |     |     |     |     | 105 |     |     |     | 110 |

| Arg | Phe | Asp | Ala | Thr | Lys | Ile | Pro | Gly | Asn | Tyr | Tyr | Ser | Phe | Tyr | Glu |
|     |     |     | 115 |     |     |     |     | 120 |     |     |     |     | 125 |

| Gly | Glu | Ala | Glu | Tyr | Asp | Gly | Cys | Val | Gly | Cys | Tyr | Gln | Tyr | Asp | Pro |
|     |     | 130 |     |     |     | 135 |     |     |     |     | 140 |

| Ile | Gln | Tyr | Arg | Lys | Thr | Cys | Asn | Asp | Arg | Ile | Tyr | Asn | Glu | Gly | Tyr |
| 145 |     |     |     |     | 150 |     |     |     |     | 155 |     |     |     |     | 160 |

| Gln | Lys | Gly | Tyr | Gly | Asp | Gly | Tyr | Gln | Ile | Gly | Tyr | His | Gln | Lys | Thr |
|     |     |     |     | 165 |     |     |     |     | 170 |     |     |     |     | 175 |

Thr Leu ( 2 ) INFORMATION FOR SEQ ID NO:3:

( i ) SEQUENCE CHARACTERISTICS:
        ( A ) LENGTH: 536 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|---|
| TGGACTAAAG | AATTTAATTG | GAGTTTGATA | AAGGGCGAAC | TCTGGGAAAT | TCTATTGATA | 60 |
| GAATACGATT | GAGTGGTTAT | GATGTTAAGT | GTGTTTTGAG | CCAAGGTGTC | CGTCAAGACA | 120 |
| TTAAGACTCA | CTATGGCCAA | CATTGTTGCA | CGATGTGCGG | GGCACGCGGC | ATCTCTGAAA | 180 |
| ACACTCACGT | GGAAGTGGGT | CATAAAGACG | GGCGCAGGGA | TGATCCAGGA | GTTTCTGATG | 240 |
| GAGATACACA | GACTGGTGAT | GATTGTCAGC | CTTTGTGTCA | AGCTTGCAAT | GACAAGAAAC | 300 |
| GCCAGATTTG | TAAAGCATTC | CAAGAGAGTG | GCCATAGATT | TGATCCAACC | ACAATTCCTG | 360 |
| GCAATCATTA | TCCTTTCTAC | GAAGGGGAGG | CCGAATATGA | TGGCTGTGTG | GGTTGTTATC | 420 |
| AACATGACCC | CACACAATAC | AGGATAGCTT | GTAATGATAG | GATATCCAAT | GAAGGGTATC | 480 |
| CCCAAGGTTA | TTATGAGGGG | TATCAAATTG | GACCCAATCC | AAAAACCACT | TTATAG | 536 |

( 2 ) INFORMATION FOR SEQ ID NO:4:

( i ) SEQUENCE CHARACTERISTICS:
        ( A ) LENGTH: 513 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|---|
| TTGGCTAAAG | AATTTAATTT | GGAGTTTGAT | AAAGGGCAAA | CTCTAGGAAA | TTCTATTGAT | 60 |
| AGAATACGCT | TGAATGGCTA | TAATACCGAA | TGTGTTTTTA | GCCAAAGTAT | CCGTCAAGAC | 120 |
| ATTAAGGCCC | ACTATAAGCA | ACAATGTTGC | ACTATGTGCG | GTGCACACGG | CAACTCTGAA | 180 |
| AACACTCAAA | TAGAGGTGGA | TCATAAAGAC | GGCCGCAAAA | ATGATTCAAG | AGTTTCTGAT | 240 |
| CCAAACGCAC | AGACTTTTGA | TGATTTTCAG | GTCTTATGCC | AAGCTTGTAA | TATTAAGAAA | 300 |
| CCCCAGATTT | GTACAGCATG | CCTAGAGCCT | CGCTATAGAC | TTGACGCAAC | CAAAATTCCT | 360 |
| GTCAATCACT | ATCCCTTTTA | TGCAGGGGAG | GCTGCATATG | ACGCCTGTGT | GGGATGCTAT | 420 |
| CAATATGACC | CCACACAATA | CAGGCAAACT | TGTAATGATG | GGATACACAA | TGAGGGGTAT | 480 |
| CCAAATGGAT | ACCATCCAAA | ACCTACTTTA | TAG | | | 513 |

( 2 ) INFORMATION FOR SEQ ID NO:5:

( i ) SEQUENCE CHARACTERISTICS:
    ( A ) LENGTH: 300 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:5:

```
TTGGCTAATG AATCTGTCTT AGAATTTGAT AAAGGGCAAA CTCCAGGAAT TTCTGTTGAT    60
AGAGTGCGCT TGAATGGCTA TAGGACTAGA GGTGTTGTGC ACCAGAGTGT CCGCCAGGAC   120
ATTAAGGTCT ACTACAAGCA ACACTGTTGC ACGATGTGCG GAGCACACGG GATCTCTGAA   180
AGCACGCAGG TAGAAGTGGG TCATAAGGAG GGTCGTAGGG ATGATCTACG AGGTTCTGAT   240
TCAAACCACA CAGACTGGCG ACGCGGCTTC CAGGCTTGTC TGCAGTGCTG GCTCACGACA   300
```

( 2 ) INFORMATION FOR SEQ ID NO:6:

( i ) SEQUENCE CHARACTERISTICS:
    ( A ) LENGTH: 501 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 1..179

( x i ) SEQUENCE DESCRIPTION: SEQ ID NO:6:

```
ATG GCG GTT GTA ATT AAA GTC GTT AAT GGC AAA ATA CAG GAA TAT GAG     48
Met Ala Val Val Ile Lys Val Val Asn Gly Lys Ile Gln Glu Tyr Glu
180             185                 190                 195

AAT GGT AAC TAT AAA AGA ACT TAT GGT AGT AAT ATC GTA GCT GCA GAT     96
Asn Gly Asn Tyr Lys Arg Thr Tyr Gly Ser Asn Ile Val Ala Ala Asp
                200                 205                 210

ACT GAT GGG CAT ATT GTT GCT GCT GTT ACT GCA AAG AGT AAA GTG GAA    144
Thr Asp Gly His Ile Val Ala Ala Val Thr Ala Lys Ser Lys Val Glu
                215                 220                 225

GAA TAT AAG AAT GGT ATT CAT AAA AGA ACC TAC TA GAAAATAGGG          189
Glu Tyr Lys Asn Gly Ile His Lys Arg Thr Tyr
                230                 235

TAATAGCGAC AAAAGCTTTG ATACATTCAG CTAGTGGGGG GGTGTTGCTG TTTTTTTGGC   249
AGTATTTTAA TGAGCAGTTG CGATAGAAAA AGTCTTTATT GGCAATAGGG GGGGTTGTCT   309
CGTTGTTTTA ATGAAGCGAT TGGTAGGGCG TGCGGTGTTA AAAAACGATC ATCGTTCAC    369
ATAGGATTGA TTAGTTGGTT TTAAGATTAT TTAATCGTG GGGTTAAGA CTTATTCATA     429
ATCAAGTTAT GTTACAATAC ATAAAATTTA ATTTTAATAA TAGCCATATT TATTTTAAAG   489
AAGCATACAA AC                                                      501
```

( 2 ) INFORMATION FOR SEQ ID NO:7:

( i ) SEQUENCE CHARACTERISTICS:
    ( A ) LENGTH: 59 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

| Met | Ala | Val | Val | Ile | Lys | Val | Val | Asn | Gly | Lys | Ile | Gln | Glu | Tyr | Glu |
|-----|-----|-----|-----|-----|-----|-----|-----|-----|-----|-----|-----|-----|-----|-----|-----|
| 1 | | | | 5 | | | | | 10 | | | | | 15 | |

| Asn | Gly | Asn | Tyr | Lys | Arg | Thr | Tyr | Gly | Ser | Asn | Ile | Val | Ala | Ala | Asp |
|-----|-----|-----|-----|-----|-----|-----|-----|-----|-----|-----|-----|-----|-----|-----|-----|
| | | | 20 | | | | | 25 | | | | | 30 | | |

| Thr | Asp | Gly | His | Ile | Val | Ala | Ala | Val | Thr | Ala | Lys | Ser | Lys | Val | Glu |
|-----|-----|-----|-----|-----|-----|-----|-----|-----|-----|-----|-----|-----|-----|-----|-----|
| | | 35 | | | | | 40 | | | | | 45 | | | |

| Glu | Tyr | Lys | Asn | Gly | Ile | His | Lys | Arg | Thr | Tyr |
|-----|-----|-----|-----|-----|-----|-----|-----|-----|-----|-----|
| 50 | | | | | 55 | | | | | |

( 2 ) INFORMATION FOR SEQ ID NO:8:

( i ) SEQUENCE CHARACTERISTICS:
        ( A ) LENGTH: 499 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

| ATGGCAAAAT | ACAGGAATAT | GAGAATGGGA | ACTATAAGAG | AACTTATGGT | AGTAGTATCG | 60 |
| TAGCTGCAGA | TACTGAGGGG | CATATGGTGG | CTGCTGTGAC | TGCAAAGGGT | GAGGTAGAAG | 120 |
| AATATAAAAC | TGGCATCCAT | AAAAGAACCT | ACTAGAAAAT | AGGGTAATAG | AGGNAAAAGC | 180 |
| TTTGAAGTAT | TCAGCTAGTG | GGGGTGTCG | CTGCNTTTCT | AGTGGTGTTT | TAATGAGNAG | 240 |
| NTGCGATAGA | AAAAGTCTCT | GNTTATAATA | GGGGGTCGTC | GGGCATTCCT | GACAATCATT | 300 |
| ACCCCTTTGA | TGTCAGGGGA | GGCTGCATTG | TGTGGCCTGT | GTGGGTTGCT | ATCTAGTTTC | 360 |
| CCCCACACAA | TATCACGTGA | ACTTGTCATG | ATGCGATACA | CAATGAGCGG | CATCAATATG | 420 |
| CATCCACATC | ATTATCCTAC | GTCACAGCCC | GTTCCCATGT | CCTATGATCG | ACTCTCGGAT | 480 |
| ACTAGATCCT | TCCCCATAC | | | | | 499 |

( 2 ) INFORMATION FOR SEQ ID NO:9:

( i ) SEQUENCE CHARACTERISTICS:
        ( A ) LENGTH: 538 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

| ATGGCAAAAT | ATAGGAATAT | GAGAATGGGA | ACTATAAGAG | AACTGATAGT | AGTAACGCTA | 60 |
| TTAATGTGCA | AGTGTCAGGT | GGTGTAGTGG | CTGTAACCAC | ATCAAAGGGT | AAAGTGGAAG | 120 |
| AATATAAGAA | TGGTATTCAT | AAAAGAACTA | CTAGAAAATA | GGGTAATAGC | GACAAAAGCT | 180 |
| TTGGCGCATT | CAGCTAGTGG | GGGTGTCGC | TGTTCTTCTG | GTGGTATTTT | CATGAGCAGC | 240 |
| TGTGATAGAA | AAAGTCTTTA | TTGGCAATAG | GGGGGTTCTC | TCGTTGTTTT | AATGAAGCGA | 300 |
| TTGGTAGGGC | GTTCGGTATT | AACAAACGAT | CATCGTTTCA | CATAGGATTG | ATCAGTTGGT | 360 |
| CTTAAGATTA | CTGTCATCGT | GGGGGCTAAC | ACCTACTCAT | AATCAAGTTA | TGTTACAATA | 420 |
| CATAGAATTT | AATTTTAATA | ATAGCCATAC | CTACCTTACA | GACGCATACA | CACCCGGATC | 480 |
| CATGAACTAC | ATCGGCTCTA | AATACAAGCT | CATTCCCTTT | ATTAAGGAAA | ATATCCAT | 538 |

( 2 ) INFORMATION FOR SEQ ID NO:10:

( i ) SEQUENCE CHARACTERISTICS:
        ( A ) LENGTH: 330 base pairs
        ( B ) TYPE: nucleic acid ( C ) STRANDEDNESS: double
( D ) TOPOLOGY: linear ( i i ) MOLECULE TYPE: DNA (genomic)

( x i ) SEQUENCE DESCRIPTION: SEQ ID NO:10:

| | | | | | | |
|---|---|---|---|---|---|---|
| AGCTAGTGGG | GGGTGTCGCT | GTCTTTCTAG | TGGTGCGTTA | ATGAGCAGTT | GCGATAGTAA | 60 |
| AAGTCCTTGT | TTATAATAGG | GGGGTGCTTC | GTTGTCTTCA | TGAAGCGATT | GGTAGGGCGT | 120 |
| GCGGTACTAC | CAAACGATCA | TTGTCTCACA | TAGGATTGAT | TGGTTGGTTT | TAGGATTATT | 180 |
| TTAATCGTGT | GTGTTAAGAC | TTACTCATGA | TCAAGTTATG | TTACTATACA | CAAAACTTAA | 240 |
| CTTTAATAAT | ACCCATACCA | CTTTCCAAGC | AGCACACCAA | CACAGATCCA | TGAACTACAT | 300 |
| CGGTTCTAAA | CACAAGCTCA | TTCCCTTTAC | | | | 330 |

( 2 ) INFORMATION FOR SEQ ID NO:11:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:11:

TTTGATAAAG GGCAAACTCT                                                             20

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:12:

TTGATAAAGG GCAAACTCTA                                                             20

( 2 ) INFORMATION FOR SEQ ID NO:13:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:13:

TGATAAAGGG CAAACTCTAG                                                             20

( 2 ) INFORMATION FOR SEQ ID NO:14:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:14:

GATAAAGGGC AAACTCTAGG                                                             20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

ATAAAGGGCA AACTCTAGGA                                                             20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

TAAAGGGCAA ACTCTAGGAA                                                             20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

AAAGGGCAAA CTCTAGGAAA                                                             20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

AAGGGCAAAC TCTAGGAAAT                                                             20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

AGGGCAAACT CTAGGAAATT                                                             20

( 2 ) INFORMATION FOR SEQ ID NO:20:

( i ) SEQUENCE CHARACTERISTICS:
        ( A ) LENGTH: 20 base pairs
        ( B ) TYPE: nucleic acid ( C ) STRANDEDNESS: double
                    ( D ) TOPOLOGY: linear ( i i ) MOLECULE TYPE: DNA (genomic)

( x i ) SEQUENCE DESCRIPTION: SEQ ID NO:20:

GGGCAAACTC TAGGAAATTC                                                                    20

( 2 ) INFORMATION FOR SEQ ID NO:21:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: DNA (genomic)

( x i ) SEQUENCE DESCRIPTION: SEQ ID NO:21:

GGCAAACTCT AGGAAATTCT                                                                    20

( 2 ) INFORMATION FOR SEQ ID NO:22:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: DNA (genomic)

( x i ) SEQUENCE DESCRIPTION: SEQ ID NO:22:

GCAAACTCTA GGAAATTCTA                                                                    20

( 2 ) INFORMATION FOR SEQ ID NO:23:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: DNA (genomic)

( x i ) SEQUENCE DESCRIPTION: SEQ ID NO:23:

CAAACTCTAG GAAATTCTAT                                                                    20

( 2 ) INFORMATION FOR SEQ ID NO:24:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: DNA (genomic)

( x i ) SEQUENCE DESCRIPTION: SEQ ID NO:24:

AAACTCTAGG AAATTCTATT                                                                    20

( 2 ) INFORMATION FOR SEQ ID NO:25:

( i ) SEQUENCE CHARACTERISTICS:
                    ( A ) LENGTH: 20 base pairs
                    ( B ) TYPE: nucleic acid
                    ( C ) STRANDEDNESS: double
                    ( D ) TOPOLOGY: linear ( i i ) MOLECULE TYPE: DNA (genomic)

39 40

-continued ( x i ) SEQUENCE DESCRIPTION: SEQ ID NO:25:

AACTCTAGGA AATTCTATTG 20

( 2 ) INFORMATION FOR SEQ ID NO:26:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

ACTCTAGGAA ATTCTATTGA 20

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:27:

CTCTAGGAAA TTCTATTGAT 20

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

TCTAGGAAAT TCTATTGATA 20

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

CTAGGAAATT CTATTGATAG 20

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:30:

TAGGAAATTC TATTGATAGA 20

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:31:

AGGAAATTCT ATTGATAGAA                        20

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:32:

GGAAATTCTA TTGATAGAAT                        20

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:33:

GAAATTCTAT TGATAGAATA                        20

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:34:

AAATTCTATT GATAGAATAC                        20

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:35:

AATTCTATTG ATAGAATACG                        20

( 2 ) INFORMATION FOR SEQ ID NO:36:

( i ) SEQUENCE CHARACTERISTICS:
        ( A ) LENGTH: 20 base pairs
        ( B ) TYPE: nucleic acid (C) STRANDEDNESS: double
(D) TOPOLOGY: linear (ii) MOLECULE TYPE: DNA (genomic)

(xi) SEQUENCE DESCRIPTION: SEQ ID NO:36:

ATTCTATTGA TAGAATACGC    20

(2) INFORMATION FOR SEQ ID NO:37:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:37:

TTCTATTGAT AGAATACGCT    20

(2) INFORMATION FOR SEQ ID NO:38:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:38:

TCTATTGATA GAATACGCTT    20

(2) INFORMATION FOR SEQ ID NO:39:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:39:

CTATTGATAG AATACGCTTG    20

(2) INFORMATION FOR SEQ ID NO:40:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:40:

TATTGATAGA ATACGCTTGA    20

(2) INFORMATION FOR SEQ ID NO:41:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

( x i ) SEQUENCE DESCRIPTION: SEQ ID NO:41:

ATTGATAGAA TACGCTTGAA                                                                                     20

( 2 ) INFORMATION FOR SEQ ID NO:42:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:42:

TTGATAGAAT ACGCTTGAAT                                                                                     20

( 2 ) INFORMATION FOR SEQ ID NO:43:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:43:

TGATAGAATA CGCTTGAATG                                                                                     20

( 2 ) INFORMATION FOR SEQ ID NO:44:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:44:

GATAGAATAC GCTTGAATGG                                                                                     20

( 2 ) INFORMATION FOR SEQ ID NO:45:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:45:

ATAGAATACG CTTGAATGGC                                                                                     20

( 2 ) INFORMATION FOR SEQ ID NO:46:

( i ) SEQUENCE CHARACTERISTICS:
    ( A ) LENGTH: 20 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:46:

TAGAATACGC TTGAATGGCT                                                                                     20

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:47:

```
AGAATACGCT  TGAATGGCTA                                              20
```

( 2 ) INFORMATION FOR SEQ ID NO:48:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:48:

```
GAATACGCTT  GAATGGCTAT                                              20
```

( 2 ) INFORMATION FOR SEQ ID NO:49:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:49:

```
CATAAAAGAA  CCTACTAGAA                                              20
```

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:50:

```
ATAAAAGAAC  CTACTAGAAA                                              20
```

( 2 ) INFORMATION FOR SEQ ID NO:51:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:51:

```
TAAAAGAACC  TACTAGAAAA                                              20
```

( 2 ) INFORMATION FOR SEQ ID NO:52:

( i ) SEQUENCE CHARACTERISTICS:
        ( A ) LENGTH: 20 base pairs
        ( B ) TYPE: nucleic acid (C) STRANDEDNESS: double
(D) TOPOLOGY: linear (ii) MOLECULE TYPE: DNA (genomic)

(xi) SEQUENCE DESCRIPTION: SEQ ID NO:52:

AAAAGAACCT ACTAGAAAAT 20

(2) INFORMATION FOR SEQ ID NO:53:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:53:

AAAGAACCTA CTAGAAAATA 20

(2) INFORMATION FOR SEQ ID NO:54:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:54:

AAGAACCTAC TAGAAAATAG 20

(2) INFORMATION FOR SEQ ID NO:55:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO:55:

AGAACCTACT AGAAAATAGG 20

(2) INFORMATION FOR SEQ ID NO:56:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:56:

GAACCTACTA GAAAATAGGG 20

(2) INFORMATION FOR SEQ ID NO:57:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: DNA (genomic)

( x i ) SEQUENCE DESCRIPTION: SEQ ID NO:57:

AACCTACTAG AAAATAGGGT 20

( 2 ) INFORMATION FOR SEQ ID NO:58:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:58:

ACCTACTAGA AAATAGGGTA 20

( 2 ) INFORMATION FOR SEQ ID NO:59:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:59:

CCTACTAGAA AATAGGGTAA 20

( 2 ) INFORMATION FOR SEQ ID NO:60:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:60:

CTACTAGAAA ATAGGGTAAT 20

( 2 ) INFORMATION FOR SEQ ID NO:61:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:61:

TACTAGAAAA TAGGGTAATA 20

( 2 ) INFORMATION FOR SEQ ID NO:62:

( i ) SEQUENCE CHARACTERISTICS:
( A ) LENGTH: 20 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:62:

ACTAGAAAAT AGGGTAATAG 20

( 2 ) INFORMATION FOR SEQ ID NO:63:

( i ) SEQUENCE CHARACTERISTICS:
        ( A ) LENGTH: 975 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:63:

```
GGGTGCGATT  TGCGTGGGCG  ATGATGTGAA  GATTGGGGCT  AATGCGGTGG  TGCTTTCAGA   60
TTTACCCACA  GGTTCTACGG  CTGTAGGCAC  TAAAGCTAAA  ACCATCACAA  AGGATCGTTA  120
ATTCTAGACA  AGCGGTTGGA  GTTTGCGCCA  TGCGGGTTAT  TTTGAGGTAA  ATTGATTAGA  180
ATTTTTTATA  GAGAGATTTT  TTAAAATGAG  TAAAAGTAAA  AAGAATTAT   TTTTGGAACT  240
CGCACAACCT  GATAAAAATG  GGGTGAGTCG  TTGGGTAAGC  GTTACAGAAT  TTTAGGAAA   300
ATACCAAGGA  TTACAGCTAG  GTAATGGGGG  AGTTGGTGCA  GGAATAGCTC  AGCTTTGGCT  360
AAAGAATTTA  ATTGGAGTT   TGATAAAGGG  CAAACTCTAG  GAAATTCTAT  TGATAGAATA  420
CGCTTGAATG  GCTATAATAC  CGAATGTGTT  TTTAACCAAA  GTATCTGTCA  AGACATTAAA  480
AACCACTATA  AGCAACAATG  TTGCGCGATG  TGTGGTGTGC  GTGGCAACTC  TGAAAACACT  540
CAAATAGAAG  TGGATCATAA  AGACGGCCGC  AAGGATGATT  CAAGAGTTTC  TGATTTAAAC  600
ACACAGACTT  TTGATGATTT  TCAGGCTTTA  TGCAAAGCTT  GTAACGATAA  GAAACGCCAG  660
ATTTGTAAAA  AATGCAAAGA  AAGTGGCTAT  AGATTTGACG  CAACAAAAAT  TCCTGGCAAT  720
TATTATTCTT  TCTATGAGGG  GGAGGCTGAA  TATGATGGTT  GTGTGGGCTG  TTATCAATAT  780
GACCCCATAC  AATACAGGAA  AACTTGTAAT  GATAGGATAT  ACAATGAAGG  GTATCAAAAA  840
GGCTATGGTG  ATGGGTATCA  AATTGGATAC  CATCAAAAAA  CTACTTTATA  GCGGTTGCAA  900
TGAACTACAT  CGGCTCTAAA  TACAAGCTCA  TTCCCTTTAT  TAAAGAAAAT  ATCCATGCGG  960
TTGTAGGCCA  TGATC                                                      975
```

( 2 ) INFORMATION FOR SEQ ID NO:64:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:64:

```
Phe  Asp  Lys  Gly  Gln  Thr  Leu
 1                 5
```

( 2 ) INFORMATION FOR SEQ ID NO:65:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:65:

```
Asp  Lys  Gly  Gln  Thr  Leu
 1                 5
```

( 2 ) INFORMATION FOR SEQ ID NO:66:

( i ) SEQUENCE CHARACTERISTICS:
    ( A ) LENGTH: 7 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:66:

Asp Lys Gly Gln Thr Leu Gly
1               5

( 2 ) INFORMATION FOR SEQ ID NO:67:

( i ) SEQUENCE CHARACTERISTICS:
    ( A ) LENGTH: 6 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:67:

Lys Gly Gln Thr Leu Gly
1               5

( 2 ) INFORMATION FOR SEQ ID NO:68:

( i ) SEQUENCE CHARACTERISTICS:
    ( A ) LENGTH: 7 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:68:

Lys Gly Gln Thr Leu Gly Asn
1               5

( 2 ) INFORMATION FOR SEQ ID NO:69:

( i ) SEQUENCE CHARACTERISTICS:
    ( A ) LENGTH: 6 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:69:

Gly Gln Thr Leu Gly Asn
1               5

( 2 ) INFORMATION FOR SEQ ID NO:70:

( i ) SEQUENCE CHARACTERISTICS:
    ( A ) LENGTH: 7 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:70:

Gly Gln Thr Leu Gly Asn Ser
1               5

( 2 ) INFORMATION FOR SEQ ID NO:71:

( i ) SEQUENCE CHARACTERISTICS:
   ( A ) LENGTH: 6 amino acids
   ( B ) TYPE: amino acid
   ( C ) STRANDEDNESS: Not Relevant
   ( D ) TOPOLOGY: linear ( i i ) MOLECULE TYPE: peptide ( x i ) SEQUENCE DESCRIPTION: SEQ ID NO:71:

Gln Thr Leu Gly Asn Ser
1               5

( 2 ) INFORMATION FOR SEQ ID NO:72:

( i ) SEQUENCE CHARACTERISTICS:
   ( A ) LENGTH: 7 amino acids
   ( B ) TYPE: amino acid
   ( C ) STRANDEDNESS: Not Relevant
   ( D ) TOPOLOGY: linear ( i i ) MOLECULE TYPE: peptide ( x i ) SEQUENCE DESCRIPTION: SEQ ID NO:72:

Gln Thr Leu Gly Asn Ser Ile
1               5

( 2 ) INFORMATION FOR SEQ ID NO:73:

( i ) SEQUENCE CHARACTERISTICS:
   ( A ) LENGTH: 6 amino acids
   ( B ) TYPE: amino acid
   ( C ) STRANDEDNESS: Not Relevant
   ( D ) TOPOLOGY: linear ( i i ) MOLECULE TYPE: peptide ( x i ) SEQUENCE DESCRIPTION: SEQ ID NO:73:

Thr Leu Gly Asn Ser Ile
1               5

( 2 ) INFORMATION FOR SEQ ID NO:74:

( i ) SEQUENCE CHARACTERISTICS:
   ( A ) LENGTH: 7 amino acids
   ( B ) TYPE: amino acid
   ( C ) STRANDEDNESS: Not Relevant
   ( D ) TOPOLOGY: linear ( i i ) MOLECULE TYPE: peptide ( x i ) SEQUENCE DESCRIPTION: SEQ ID NO:74:

Thr Leu Gly Asn Ser Ile Asp
1               5

( 2 ) INFORMATION FOR SEQ ID NO:75:

( i ) SEQUENCE CHARACTERISTICS:
   ( A ) LENGTH: 6 amino acids
   ( B ) TYPE: amino acid
   ( C ) STRANDEDNESS: Not Relevant
   ( D ) TOPOLOGY: linear ( i i ) MOLECULE TYPE: peptide ( x i ) SEQUENCE DESCRIPTION: SEQ ID NO:75:

Leu Gly Asn Ser Ile Asp
1               5

( 2 ) INFORMATION FOR SEQ ID NO:76:

( i ) SEQUENCE CHARACTERISTICS:
    ( A ) LENGTH: 7 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:76:

Leu Gly Asn Ser Ile Asp Arg
 1               5

( 2 ) INFORMATION FOR SEQ ID NO:77:

( i ) SEQUENCE CHARACTERISTICS:
    ( A ) LENGTH: 6 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:77:

Gly Asn Ser Ile Asp Arg
 1               5

( 2 ) INFORMATION FOR SEQ ID NO:78:

( i ) SEQUENCE CHARACTERISTICS:
    ( A ) LENGTH: 7 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:78:

Gly Asn Ser Ile Asp Arg Ile
 1               5

( 2 ) INFORMATION FOR SEQ ID NO:79:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:79:

Asn Ser Ile Asp Arg Ile Arg
 1               5

( 2 ) INFORMATION FOR SEQ ID NO:80:

( i ) SEQUENCE CHARACTERISTICS:
    ( A ) LENGTH: 7 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:80:

Asn Ser Ile Asp Arg Ile Arg
 1               5

( 2 ) INFORMATION FOR SEQ ID NO:81:

( i ) SEQUENCE CHARACTERISTICS:
  ( A ) LENGTH: 6 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:81:

Ser Ile Asp Arg Ile Arg
1               5

( 2 ) INFORMATION FOR SEQ ID NO:82:

( i ) SEQUENCE CHARACTERISTICS:
  ( A ) LENGTH: 7 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:82:

Ser Ile Asp Arg Ile Arg Leu
1               5

( 2 ) INFORMATION FOR SEQ ID NO:83:

( i ) SEQUENCE CHARACTERISTICS:
  ( A ) LENGTH: 6 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:83:

Ile Asp Arg Ile Arg Leu
1               5

( 2 ) INFORMATION FOR SEQ ID NO:84:

( i ) SEQUENCE CHARACTERISTICS:
  ( A ) LENGTH: 7 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:84:

Ile Asp Arg Ile Arg Leu Asn
1               5

( 2 ) INFORMATION FOR SEQ ID NO:85:

( i ) SEQUENCE CHARACTERISTICS:
  ( A ) LENGTH: 6 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:85:

Asp Arg Ile Arg Leu Asn
1               5

( 2 ) INFORMATION FOR SEQ ID NO:86:

( i ) SEQUENCE CHARACTERISTICS:
  ( A ) LENGTH: 7 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:86:

Asp Arg Ile Arg Leu Asn Gly
1               5

( 2 ) INFORMATION FOR SEQ ID NO:87:

( i ) SEQUENCE CHARACTERISTICS:
  ( A ) LENGTH: 6 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:87:

Arg Ile Arg Leu Asn Gly
1               5

( 2 ) INFORMATION FOR SEQ ID NO:88:

( i ) SEQUENCE CHARACTERISTICS:
  ( A ) LENGTH: 7 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:88:

Arg Ile Arg Leu Asn Gly Tyr
1               5

( 2 ) INFORMATION FOR SEQ ID NO:89:

( i ) SEQUENCE CHARACTERISTICS:
  ( A ) LENGTH: 6 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:89:

Ile Arg Leu Asn Gly Tyr
1               5

( 2 ) INFORMATION FOR SEQ ID NO:90:

( i ) SEQUENCE CHARACTERISTICS:
  ( A ) LENGTH: 7 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:90:

Ile Arg Leu Asn Gly Tyr Asn
1               5

( 2 ) INFORMATION FOR SEQ ID NO:91:

( i ) SEQUENCE CHARACTERISTICS:
    ( A ) LENGTH: 6 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:91:

Arg Leu Asn Gly Tyr Asn
1                  5

( 2 ) INFORMATION FOR SEQ ID NO:92:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:92:

Arg Leu Asn Gly Tyr Asn Thr
1                  5

( 2 ) INFORMATION FOR SEQ ID NO:93:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:93:

Leu Asn Gly Tyr Asn Thr
1                  5

( 2 ) INFORMATION FOR SEQ ID NO:94:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:94:

Leu Asn Gly Tyr Asn Thr Glu
1                  5

( 2 ) INFORMATION FOR SEQ ID NO:95:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:95:

Asn Gly Tyr Asn Thr Glu
1                  5

( 2 ) INFORMATION FOR SEQ ID NO:96:

( i ) SEQUENCE CHARACTERISTICS:
  ( A ) LENGTH: 7 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:96:

Asn Gly Tyr Asn Thr Glu Cys
1               5

( 2 ) INFORMATION FOR SEQ ID NO:97:

( i ) SEQUENCE CHARACTERISTICS:
  ( A ) LENGTH: 6 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:97:

Gly Tyr Asn Thr Glu Cys
1           5

( 2 ) INFORMATION FOR SEQ ID NO:98:

( i ) SEQUENCE CHARACTERISTICS:
  ( A ) LENGTH: 7 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:98:

Gly Tyr Asn Thr Glu Cys Val
1           5

( 2 ) INFORMATION FOR SEQ ID NO:99:

( i ) SEQUENCE CHARACTERISTICS:
  ( A ) LENGTH: 6 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:99:

Tyr Asn Thr Glu Cys Val
1           5

( 2 ) INFORMATION FOR SEQ ID NO:100:

( i ) SEQUENCE CHARACTERISTICS:
  ( A ) LENGTH: 7 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:100:

Tyr Asn Thr Glu Cys Val Phe
1           5

( 2 ) INFORMATION FOR SEQ ID NO:101:

(i) SEQUENCE CHARACTERISTICS:
  (A) LENGTH: 170 amino acids
  (B) TYPE: amino acid
  (C) STRANDEDNESS: Not Relevant
  (D) TOPOLOGY: linear (ii) MOLECULE TYPE: peptide (xi) SEQUENCE DESCRIPTION: SEQ ID NO:101:

```
Leu Ala Lys Glu Phe Asn Leu Glu Phe Asp Lys Gly Gln Thr Leu Gly
  1           5                  10                  15
Asn Ser Ile Asp Arg Ile Arg Leu Asn Gly Tyr Asn Thr Glu Cys Val
             20                  25                  30
Phe Ser Gln Ser Ile Arg Gln Asp Ile Lys Ala His Tyr Lys Gln Gln
         35                  40                  45
Cys Cys Thr Met Cys Gly Ala His Gly Asn Ser Glu Asn Thr Gln Ile
     50                  55                  60
Glu Val Asp His Lys Asp Gly Arg Lys Asn Asp Ser Arg Val Ser Asp
 65                  70                  75                  80
Pro Asn Ala Gln Thr Phe Asp Asp Phe Gln Val Leu Cys Gln Ala Cys
             85                  90                  95
Asn Ile Lys Lys Pro Gln Ile Cys Thr Ala Cys Leu Glu Pro Arg Tyr
            100                 105                 110
Arg Leu Asp Ala Thr Lys Ile Pro Val Asn His Tyr Pro Phe Tyr Ala
            115                 120                 125
Gly Glu Ala Ala Tyr Asp Ala Cys Val Gly Cys Tyr Gln Tyr Asp Pro
        130                 135                 140
Thr Gln Tyr Arg Gln Thr Cys Asn Asp Gly Ile His Asn Glu Gly Tyr
145                 150                 155                 160
Pro Asn Gly Tyr His Pro Lys Pro Thr Leu
                165                 170
```